Figure 2:
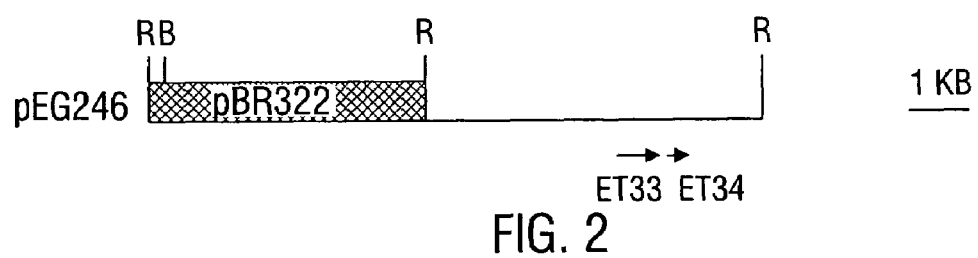

US007504229B2

(12) United States Patent
Donovan et al.

(10) Patent No.: US 7,504,229 B2
(45) Date of Patent: Mar. 17, 2009

(54) **METHODS FOR DETECTING *BACILLUS THURINGIENSIS* CRYET33 AND CRYET34 POLYPEPTIDES**

(75) Inventors: William P. Donovan, Levittown, PA (US); Judith C. Donovan, Levittown, PA (US); Annette C. Slaney, Hamilton Square, NJ (US)

(73) Assignee: Monsanto Technology LLC, St. Louis, MO (US)

( * ) Notice: Subject to any disclaimer, the term of this patent is extended or adjusted under 35 U.S.C. 154(b) by 480 days.

(21) Appl. No.: 11/231,104

(22) Filed: Sep. 20, 2005

(65) Prior Publication Data

US 2006/0051822 A1 Mar. 9, 2006

Related U.S. Application Data

(60) Division of application No. 09/949,972, filed on Sep. 10, 2001, now Pat. No. 6,949,626, which is a division of application No. 09/147,992, filed as application No. PCT/US97/17600 on Sep. 24, 1997, now Pat. No. 6,326,351, which is a continuation-in-part of application No. 08/718,905, filed on Sep. 24, 1996, now Pat. No. 6,063,756.

(51) Int. Cl.
*G01N 33/554* (2006.01)
*C12P 21/08* (2006.01)

(52) U.S. Cl. ................ 435/7.32; 530/387.1; 530/388.1; 530/388.4

(58) Field of Classification Search ................ 435/7.32; 530/387.1, 388.1, 388.4
See application file for complete search history.

(56) References Cited

U.S. PATENT DOCUMENTS

| | | | | |
|---|---|---|---|---|
| 4,766,203 | A | 8/1988 | Krieg et al. | 530/370 |
| 4,771,131 | A | 9/1988 | Herrnstadt et al. | 536/27 |
| 4,797,279 | A | 1/1989 | Karamata et al. | 424/93 |
| 4,910,016 | A | 3/1990 | Gaertner et al. | 424/93 |
| 4,966,765 | A | 10/1990 | Payne et al. | 424/93 |
| 4,996,155 | A | 2/1991 | Sick et al. | 435/252.3 |
| 4,999,192 | A | 3/1991 | Payne et al. | 424/93 |
| 5,006,336 | A | 4/1991 | Payne | 424/93 |
| 5,024,837 | A | 6/1991 | Donovan et al. | 424/93 |
| 5,071,654 | A | 12/1991 | English | 424/405 |
| 5,143,905 | A | 9/1992 | Sivasubramanian et al. | 514/21 |
| 5,173,409 | A | 12/1992 | English | 435/71.1 |
| 5,187,091 | A | 2/1993 | Donovan et al. | 435/240.4 |
| 5,264,364 | A | 11/1993 | Donovan et al. | 435/252.5 |
| 5,286,486 | A | 2/1994 | Payne et al. | 424/93 |
| 5,308,760 | A * | 5/1994 | Brown et al. | 435/69.1 |
| 5,338,544 | A | 8/1994 | Donovan | 424/93.2 |
| 5,356,623 | A | 10/1994 | von Tersch et al. | 424/93.2 |
| 5,378,625 | A | 1/1995 | Donovan et al. | 435/252.5 |
| 5,382,429 | A | 1/1995 | Donovan et al. | 424/94.461 |
| 5,384,253 | A | 1/1995 | Krzyzek et al. | 435/172.3 |
| 5,441,884 | A | 8/1995 | Baum | 435/252.31 |

FOREIGN PATENT DOCUMENTS

| | | | |
|---|---|---|---|
| EP | 0318143 | A2 | 10/1988 |
| EP | 0324254 | A1 | 12/1988 |
| EP | 0382990 | A1 | 2/1989 |
| WO | WO89/07605 | | 8/1989 |
| WO | WO90/13651 | | 11/1990 |
| WO | WO91/07481 | | 5/1991 |
| WO | WO91/14778 | | 10/1991 |
| WO | WO92/13954 | | 8/1992 |
| WO | WO94/13785 | | 6/1994 |
| WO | WO94/16079 | | 7/1994 |
| WO | WO95/02693 | | 1/1995 |
| WO | WO95/06730 | | 3/1995 |
| WO | WO95/30752 | | 11/1995 |
| WO | WO95/30753 | | 11/1995 |
| WO | WO95/35378 | | 12/1995 |

OTHER PUBLICATIONS

Donovan et al., "Characterization of two genes encoding *Bacillus thuringiensis* insecticidal crystal proteins toxic to *coleoptera* species," *Applied and Environmental Microbiology*, 58(12):3921-3927, 1992.

Donovan et al., "Isolation and characterization of EG2158, a new strain of *Bacillus thuringiensis* toxic to coleopteran larvae, and nucleotide sequence of the toxin gene," *Mol Gen Genet*, 214:365-372, 1988.

Lambert al., "A *Bacillus thuringiensis* insecticidal crystal protein with a high activity against members of the family noctuidae," *Applied and Environmental Microbiology*, 62(1):80-86, 1996.

Lambert et al., "Novel *Bacillus thuringiensis* insecticidal crystal protein with a silent activity against coleopteran larvae," *Applied and Environmental Microbiology*, 58(8):2536-2542, 1992.

Lambert et al., "Nucleotide sequence of gene *crylIID* encoding a novel coleopteran-active crystal protein from strain BTI109P of *Bacillus thuringiensis* subsp. *kurstak*," *Gene*, 110:131-132, 1992.

(Continued)

*Primary Examiner*—Brandon J Fetterolf
(74) *Attorney, Agent, or Firm*—Timothy K. Ball, Esq.; Howrey LLP

(57) ABSTRACT

Disclosed are *Bacillus thuringiensis* strains comprising novel crystal proteins which exhibit insecticidal activity against coleopteran insects including red flour beetle larvae (*Tribolium castaneum*) and Japanese beetle larvae (*Popillia japonica*). Also disclosed are novel *B. thuringiensis* crystal toxin genes, designated cryET33 and cryET34, which encode the colepteran-toxic crystal proteins, CryET33 (29-kDa) crystal protein, and the cryET34 gene encodes the 14-kDa CryET34 crystal protein. The CryET33 and CryET34 crystal proteins are toxic to red flour beetle larvae and Japanese beetle larvae. Also disclosed are methods of making and using transgenic cells comprising the novel nucleic acid sequences of the invention.

7 Claims, 4 Drawing Sheets

OTHER PUBLICATIONS

Sick et al., "Nucleotide sequence of a coleopteran-active toxin gene from a new isolate of *Bacillus thuringiensis* subsp. *tolworthi*," *Nucleic Acids Research*, 18(5):1305, 1989.

Von Tersch et al., "Membrane-Permeabilizing Activities of *Bacillus thuringiensis* Coleopteran-Active Toxin CryIIIB2 and CryIIIB2 Domain I Peptide," *Applied and Environmental Microbiology*, 60(10):3711-3717, 1994.

Ely, "The engineering of plants to express *Bacillus thuringiensis* δ-endotoxins," In: *Bacillus thuringiensis, An Environmental Biopesticide: Theory and Practice*, Entwistle, et al., Eds., Chichester, Wiley & Sons, pp. 105-124, 1993.

International Search Report dated Feb. 20, 1998 (PCT/US97/17600) (MECO:203P).

Johnson et al., "Insecticidal activity of EG4961, a novel strain of *Bacillus thuringiensis* toxic to larvae and adults of Southern Corn Rootworm (Coleoptera: Chrysomelidae) and Colorado Potato Beetle (Coleoptera: Chrysomelidae)," *J. Economic Entomol.*, 86(2):330-333, 1993.

Cidaria et al., "A novel strain of *Bacillus-thuringiensis* (NCIMB 40152) active against coleopteran insects," *FEMS Microbiology Letters*, 81:129-134, 1991.

Cody et al., "Purification and Crystallization of Insecticidal δ-Endotoxin CyrIIIB2 From *Bacillus thuringiensis*," *Proteins: Structure, Function and Genetics*, 14:324, 1992.

\* cited by examiner

```
         10        20        30        40        50        60
TGTTAAAATTTTTATAAATTCTTAACATTTGATGTTCAAGTAAGAATTACATTGAACTTT 70        80        90       100       110       120
AATTTGTATACATCATTTGTTTAGAATTAATCCAACTACTTAAGTTGGTAAATAAAATAC 130       140       150       160       170       180
AGGAGGTATTTAAATATGGGAATTATTAATATCCAAGATGAAATTAATAATTACATGAAA
                    MetGlyIleIleAsnIleGlnAspGluIleAsnAsnTyrMetLys 190       200       210       220       230       240
GAGGTATATGGTGCAACAACTGTTAAAAGCACATACGATCCCTCATTCAAAGTATTTAAT
GluValTyrGlyAlaThrThrValLysSerThrTyrAspProSerPheLysValPheAsn 250       260       270       280       290       300
GAATCTGTGACACCCCAATTCACTGAAATTCCAACAGAACCTGTAAATAATCAATTAACT
GluSerValThrProGlnPheThrGluIleProThrGluProValAsnAsnGlnLeuThr 310       320       330       340       350       360
ACAAAAAGAGTAGATAATACGGGTAGTTACCCAGTAGAAAGTACTGTATCGTTCACATGG
ThrLysArgValAspAsnThrGlySerTyrProValGluSerThrValSerPheThrTrp 370       380       390       400       410       420
ACGGAAACCCATACAGAAACAAGTGCAGTAACTGAGGGAGTGAAAGCCGGCACCTCAATA
ThrGluThrHisThrGluThrSerAlaValThrGluGlyValLysAlaGlyThrSerIle 430       440       450       460       470       480
AGTACTAAACAATCTTTTAAATTTGGTTTTTGTTAACTCTGATGTTACTTTAACGGTATCA
SerThrLysGlnSerPheLysPheGlyPheValAsnSerAspValThrLeuThrValSer 490       500       510       520       530       540
GCAGAATATAATTATAGTACAACAAATACAACTACAACAACAGAAACACACACCTGGTCA
AlaGluTyrAsnTyrSerThrThrAsnThrThrThrThrThrGluThrHisThrTrpSer 550       560       570       580       590       600
GATTCAACAAAAGTAACTATTCCTCCCAAAACTTATGTGGAGGCTGCATACATTATCCAA
AspSerThrLysValThrIleProProLysThrTyrValGluAlaAlaTyrIleIleGln
```

FIG. 1A

```
             610       620       630       640       650       660
         AATGGAACATATAATGTTCCGGTTAATGTAGAATGTGATATGAGTGGAACTTTATTTTGT
         AsnGlyThrTyrAsnValProValAsnValGluCysAspMetSerGlyThrLeuPheCys 670       680       690       700       710       720
         AGAGGGTATAGAGATGGTGCGCTTATTGCAGCAGTTTATGTTTCTGTAGCGGATTTAGCA
         ArgGlyTyrArgAspGlyAlaLeuIleAlaAlaValTyrValSerValAlaAspLeuAla 730       740       750       760       770       780
         GATTACAATCCAAATTTAAATCTTACAAATAAAGGGGATGGAATTGCTCACTTTAAAGGT
         AspTryAsnProAsnLeuAsnLeuThrAsnLysGlyAspGlyIleAlaHisPheLysGly 790       800       810       820       830       840
         TCGGGTTTTATAGAGGGTGCACAAGGCTTGCGAAGCATTATTCAGGTTACAGAATATCCA
         SerGlyPheIleGluGlyAlaGlnGlyLeuArgSerIleIleGlnValThrGluTyrPro 850       860       870       880       890       900
         CTAGATGATAATAAAGGTCGCTCGACACCAATAACTTATTTAATAAATGGTTCATTAGCA
         LeuAspAspAsnLysGlyArgSerThrProIleThrTyrLeuIleAsnGlySerLeuAla 910       920       930       940       950       960
         CCAAATGTTACATTAAAAAATAGCAACATAAAATTTTAATAAATAACAAAAAAGGAAGGT
         ProAsnValThrLeuLysAsnSerAsnIleLysPheEndEnd 970       980       990      1000      1010      1020
         TGATAAAAATGACAGTATATAACGCAACTTTCACCATTAATTTCTATAATGAAGGAGAAT
                      MetThrValTyrAsnAlaThrPheThrIleAsnPheTyrAsnGluGlyGluT 1030      1040      1050      1060      1070      1080
         GGGGGGGGGCCAGAACCATATGGTTATATAAAAGCATATCTTACAAATCCAGATCATGATT
         rpGlyGlyProGluProTyrGlyTyrIleLysAlaTyrLeuThrAsnProAspHisAspP
```

FIG. 1B

```
          1090      1100      1110      1120      1130      1140
        TTGAAATTTGGAAACAAGATGATTGGGGGAAAAGTACTCCTGAGAGAAGTACTTATACGC
        heGluIleTrpLysGlnAspAspTrpGlyLysSerThrProGluArgSerThrTyrThrG 1150      1160      1170      1180      1190      1200
        AAACGATTAAAATAAGTAGCGACACTGGTTCCCCTATAAACCAAATGTGTTTTTATGGTG
        lnThrIleLysIleSerSerAspThrGlySerProIleAsnGlnMetCysPheTyrGlyA 1210      1220      1230      1240      1250      1260
        ATGTGAAAGAATACGACGTAGGAAATGCAGATGATATTCTCGCTTATCCAAGTCAAAAAG
        spValLysGluTyrAspValGlyAsnAlaAspAspIleLeuAlaTyrProSerGlnLysV 1270      1280      1290      1300      1310      1320
        TATGCAGTACACCTGGTGTAACAGTACGACTTGATGGCGATGAGAAAGGTTCTTATGTGA
        alCysSerThrProGlyValThrValArgLeuAspGlyAspGluLysGlySerTyrValT 1330      1340      1350      1360      1370      1380
        CAATTAAGTATTCCTTGACTCCAGCATAAATTTCAAATAAATCATTGCTTAACATATTTG
        hrIleLysTyrSerLeuThrProAlaEnd 1390      1400      1410      1420      1430      1440
        AGGACCATATCTTTCCTGAAATGCTAGCTCTATCTTTTACAACCTTCAATCCTCAAAATT 1450      1460      1470      1480      1490      1500
        CTCTAAACTAGAATCATAAAATTTTATATTCTCTTATTATGTTGCACTATTCTAAATGGG 1510      1520      1530      1540      1550      1560
        GAATCCAACATGCTCATCTTCAAAAATAATAATAAAAACTTTCAATCTATTTAGAAATGC 1570      1580      1590
        AACGAATCATTAATACGCATTATATATAGT
```

FIG. 1C

```
                        SEQUENCE LISTING

<160> NUMBER OF SEQ ID NOS: 11

<210> SEQ ID NO 1
<211> LENGTH: 807
<212> TYPE: DNA
<213> ORGANISM: Bacillus Thuringiensis

<400> SEQUENCE: 1
atgggaatta ttaatatcca agatgaaatt aataattaca tgaaagaggt atatggtgca      60
acaactgtta aaagcacata cgatccctca ttcaaagtat ttaatgaatc tgtgacaccc     120
caattcactg aaattccaac agaacctgta aataatcaat taactacaaa aagagtagat     180
aatacgggta gttacccagt agaaagtact gtatcgttca catggacgga aacccataca     240
gaaacaagtg cagtaactga gggagtgaaa gccggcacct caataagtac taaacaatct     300
tttaaatttg gttttgttaa ctctgatgtt actttaacgg tatcagcaga atataattat     360
agtacaacaa atacaactac aacaacagaa acacacacct ggtcagattc aacaaaagta     420
actattcctc ccaaaactta tgtggaggct gcatacatta tccaaaatgg aacatataat     480
gttccggtta atgtagaatg tgatatgagt ggaactttat tttgtagagg gtatagagat     540
ggtgcgctta ttgcagcagt ttatgtttct gtagcggatt tagcagatta caatccaaat     600
ttaaatctta caaataaagg ggatggaatt gctcacttta aaggttcggg ttttatagag     660
ggtgcacaag gcttgcgaag cattattcag gttacagaat atccactaga tgataataaa     720
ggtcgctcga caccaataac ttatttaata aatggttcat tagcaccaaa tgttacatta     780
```

```
                            aaaaatagca acataaaatt ttaataa                    807
```

<210> SEQ ID NO 2
<211> LENGTH: 381
<212> TYPE: DNA
<213> ORGANISM: Bacillus Thuringiensis

<400> SEQUENCE: 2

```
atgacagtat ataacgcaac tttcaccatt aatttctata atgaaggaga atgggggggg     60
ccagaaccat atggttatat aaaagcatat cttacaaatc cagatcatga ttttgaaatt    120
tggaaacaag atgattgggg gaaaagtact cctgagagaa gtacttatac gcaaacgatt    180
aaaataagta gcgacactgg ttcccctata aaccaaatgt gttttatgg tgatgtgaaa     240 gaatacgacg taggaaatgc agatgatatt ctcgcttatc caagtcaaaa agtatgcagt    300
acacctggtg taacagtacg acttgatggc gatgagaaag gttcttatgt gacaattaag    360
tattccttga ctccagcata a                                              381
```

<210> SEQ ID NO 3
<211> LENGTH: 267
<212> TYPE: PRT
<213> ORGANISM: Bacillus Thuringiensis

<400> SEQUENCE: 3

```
Met Gly Ile Ile Asn Ile Gln Asp Glu Ile Asn Asn Tyr Met Lys Glu
 1               5                  10                  15

Val Tyr Gly Ala Thr Thr Val Lys Ser Thr Tyr Asp Pro Ser Phe Lys
             20                  25                  30

Val Phe Asn Glu Ser Val Thr Pro Gln Phe Thr Glu Ile Pro Thr Glu
         35                  40                  45

Pro Val Asn Asn Gln Leu Thr Thr Lys Arg Val Asp Asn Thr Gly Ser
     50                  55                  60

Tyr Pro Val Glu Ser Thr Val Ser Phe Thr Trp Glu Thr His Thr
 65                  70                  75                  80

Glu Thr Ser Ala Val Thr Glu Gly Val Lys Ala Gly Thr Ser Ile Ser
                 85                  90                  95

Thr Lys Gln Ser Phe Lys Phe Gly Phe Val Asn Ser Asp Val Thr Leu
            100                 105                 110

Thr Val Ser Ala Glu Tyr Asn Tyr Ser Thr Thr Asn Thr Thr Thr Thr
        115                 120                 125

Thr Glu Thr His Thr Trp Ser Asp Ser Thr Lys Val Thr Ile Pro Pro
    130                 135                 140

Lys Thr Tyr Val Glu Ala Ala Tyr Ile Ile Gln Asn Gly Thr Tyr Asn
145                 150                 155                 160

Val Pro Val Asn Val Glu Cys Asp Met Ser Gly Thr Leu Phe Cys Arg
                165                 170                 175

Gly Tyr Arg Asp Gly Ala Leu Ile Ala Ala Val Tyr Val Ser Val Ala
            180                 185                 190

Asp Leu Ala Asp Tyr Asn Pro Asn Leu Asn Leu Thr Asn Lys Gly Asp
        195                 200                 205

Gly Ile Ala His Phe Lys Gly Ser Gly Phe Ile Glu Gly Ala Gln Gly
    210                 215                 220

Leu Arg Ser Ile Ile Gln Val Thr Glu Tyr Pro Leu Asp Asp Asn Lys
225                 230                 235                 240

Gly Arg Ser Thr Pro Ile Thr Tyr Leu Ile Asn Gly Ser Leu Ala Pro
                245                 250                 255
```

```
Asn Val Thr Leu Lys Asn Ser Asn Ile Lys Phe
        260                 265

<210> SEQ ID NO 4
<211> LENGTH: 126
<212> TYPE: PRT
<213> ORGANISM: Bacillus Thuringiensis

<400> SEQUENCE: 4

Met Thr Val Tyr Asn Ala Thr Phe Thr Ile Asn Phe Tyr Asn Glu Gly
1               5                   10                  15

Glu Trp Gly Gly Pro Glu Pro Tyr Gly Tyr Ile Lys Ala Tyr Leu Thr
            20                  25                  30

Asn Pro Asp His Asp Phe Glu Ile Trp Lys Gln Asp Asp Trp Gly Lys
        35                  40                  45

Ser Thr Pro Glu Arg Ser Thr Tyr Thr Gln Thr Ile Lys Ile Ser Ser
    50                  55                  60

Asp Thr Gly Ser Pro Ile Asn Gln Met Cys Phe Tyr Gly Asp Val Lys
65                  70                  75                  80

Glu Tyr Asp Val Gly Asn Ala Asp Asp Ile Leu Ala Tyr Pro Ser Gln
                85                  90                  95

Lys Val Cys Ser Thr Pro Gly Val Thr Val Arg Leu Asp Gly Asp Glu
            100                 105                 110

Lys Gly Ser Tyr Val Thr Ile Lys Tyr Ser Leu Thr Pro Ala
        115                 120                 125

<210> SEQ ID NO 5
<211> LENGTH: 20
<212> TYPE: PRT
<213> ORGANISM: Bacillus Thuringiensis

<400> SEQUENCE: 5

Gly Ile Ile Asn Ile Gln Asp Glu Ile Asn Asn Tyr Met Lys Glu Val
1               5                   10                  15

Tyr Gly Ala Thr
            20

<210> SEQ ID NO 6
<211> LENGTH: 20
<212> TYPE: PRT
<213> ORGANISM: Bacillus Thuringiensis

<400> SEQUENCE: 6

Thr Val Tyr Asn Val Thr Phe Thr Ile Lys Phe Tyr Asn Glu Gly Glu
1               5                   10                  15

Trp Gly Gly Pro
            20

<210> SEQ ID NO 7
<211> LENGTH: 11
<212> TYPE: PRT
<213> ORGANISM: Bacillus Thuringiensis

<400> SEQUENCE: 7

Met Gly Ile Ile Asn Ile Gln Asp Glu Ile Asn
1               5                   10

<210> SEQ ID NO 8
<211> LENGTH: 8
<212> TYPE: PRT
```

<213> ORGANISM: Bacillus Thuringiensis

<400> SEQUENCE: 8

Tyr Met Lys Glu Val Tyr Gly Ala
1               5

<210> SEQ ID NO 9
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 9
atgggaatta ttaatattca agatgaaatt aat                                33

<210> SEQ ID NO 10
<211> LENGTH: 56
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: modified_base
<222> LOCATION: (34)..(36)
<223> OTHER INFORMATION: N = Inosine
<220> FEATURE:
<221> NAME/KEY: misc_feature
<222> LOCATION: (34)..(36)
<223> OTHER INFORMATION: N = Inosine

<400> SEQUENCE: 10
atgggaatta ttaatattca agatgaaatt aatnnntata tgaaagaagt atatgg       56

<210> SEQ ID NO 11
<211> LENGTH: 1590
<212> TYPE: DNA
<213> ORGANISM: Bacillus Thuringiensis
<220> FEATURE:
<221> NAME/KEY: CDS
<222> LOCATION: (136)..(939)
<220> FEATURE:
<221> NAME/KEY: CDS
<222> LOCATION: (969)..(1349)

<400> SEQUENCE: 11

```
tgttaaaatt tttataaatt cttaacattt gatgttcaag taagaattac attgaacttt          60
aatttgtata catcatttgt ttagaattaa tccaactact taagttggta aataaaatac         120
aggaggtatt taaat atg gga att att aat atc caa gat gaa att aat aat         171
               Met Gly Ile Ile Asn Ile Gln Asp Glu Ile Asn Asn
                 1               5                  10 tac atg aaa gag gta tat ggt gca aca act gtt aaa agc aca tac gat         219
Tyr Met Lys Glu Val Tyr Gly Ala Thr Thr Val Lys Ser Thr Tyr Asp
        15                  20                  25 ccc tca ttc aaa gta ttt aat gaa tct gtg aca ccc caa ttc act gaa         267
Pro Ser Phe Lys Val Phe Asn Glu Ser Val Thr Pro Gln Phe Thr Glu
    30                  35                  40 att cca aca gaa cct gta aat aat caa tta act aca aaa aga gta gat         315
Ile Pro Thr Glu Pro Val Asn Asn Gln Leu Thr Thr Lys Arg Val Asp
45                  50                  55                  60 aat acg ggt agt tac cca gta gaa agt act gta tcg ttc aca tgg acg         363
Asn Thr Gly Ser Tyr Pro Val Glu Ser Thr Val Ser Phe Thr Trp Thr
                65                  70                  75 gaa acc cat aca gaa aca agt gca gta act gag gga gtg aaa gcc ggc         411
Glu Thr His Thr Glu Thr Ser Ala Val Thr Glu Gly Val Lys Ala Gly
```

-continued

|  |  |  |  |  |  |  |  |  |  |  |  |  |  |  |  |
|---|---|---|---|---|---|---|---|---|---|---|---|---|---|---|---|
|  |  | 80 |  |  |  | 85 |  |  |  | 90 |  |  |  |  |  |
| acc | tca | ata | agt | act | aaa | caa | tct | ttt | aaa | ttt | ggt | ttt | gtt | aac tct | 459 |
| Thr | Ser | Ile | Ser | Thr | Lys | Gln | Ser | Phe | Lys | Phe | Gly | Phe | Val | Asn Ser |  |
|  |  | 95 |  |  |  | 100 |  |  |  | 105 |  |  |  |  |  |
| gat | gtt | act | tta | acg | gta | tca | gca | gaa | tat | aat | tat | agt | aca | aca aat | 507 |
| Asp | Val | Thr | Leu | Thr | Val | Ser | Ala | Glu | Tyr | Asn | Tyr | Ser | Thr | Thr Asn |  |
|  | 110 |  |  |  |  | 115 |  |  |  |  | 120 |  |  |  |  |
| aca | act | aca | aca | aca | gaa | aca | cac | acc | tgg | tca | gat | tca | aca | aaa gta | 555 |
| Thr | Thr | Thr | Thr | Thr | Glu | Thr | His | Thr | Trp | Ser | Asp | Ser | Thr | Lys Val |  |
| 125 |  |  |  |  |  | 130 |  |  |  |  | 135 |  |  | 140 |  |
| act | att | cct | ccc | aaa | act | tat | gtg | gag | gct | gca | tac | att | atc | caa aat | 603 |
| Thr | Ile | Pro | Pro | Lys | Thr | Tyr | Val | Glu | Ala | Ala | Tyr | Ile | Ile | Gln Asn |  |
|  |  |  |  | 145 |  |  |  |  | 150 |  |  |  |  | 155 |  |
| gga | aca | tat | aat | gtt | ccg | gtt | aat | gta | gaa | tgt | gat | atg | agt | gga act | 651 |
| Gly | Thr | Tyr | Asn | Val | Pro | Val | Asn | Val | Glu | Cys | Asp | Met | Ser | Gly Thr |  |
|  |  |  | 160 |  |  |  |  | 165 |  |  |  |  | 170 |  |  |
| tta | ttt | tgt | aga | ggg | tat | aga | gat | ggt | gcg | ctt | att | gca | gca | gtt tat | 699 |
| Leu | Phe | Cys | Arg | Gly | Tyr | Arg | Asp | Gly | Ala | Leu | Ile | Ala | Ala | Val Tyr |  |
|  |  | 175 |  |  |  |  | 180 |  |  |  |  | 185 |  |  |  |
| gtt | tct | gta | gcg | gat | tta | gca | gat | tac | aat | cca | aat | tta | aat | ctt aca | 747 |
| Val | Ser | Val | Ala | Asp | Leu | Ala | Asp | Tyr | Asn | Pro | Asn | Leu | Asn | Leu Thr |  |
|  | 190 |  |  |  |  | 195 |  |  |  |  | 200 |  |  |  |  |
| aat | aaa | ggg | gat | gga | att | gct | cac | ttt | aaa | ggt | tcg | ggt | ttt | ata gag | 795 |
| Asn | Lys | Gly | Asp | Gly | Ile | Ala | His | Phe | Lys | Gly | Ser | Gly | Phe | Ile Glu |  |
| 205 |  |  |  |  |  | 210 |  |  |  |  | 215 |  |  | 220 |  |
| ggt | gca | caa | ggc | ttg | cga | agc | att | att | cag | gtt | aca | gaa | tat | cca cta | 843 |
| Gly | Ala | Gln | Gly | Leu | Arg | Ser | Ile | Ile | Gln | Val | Thr | Glu | Tyr | Pro Leu |  |
|  |  |  |  | 225 |  |  |  |  | 230 |  |  |  |  | 235 |  |
| gat | gat | aat | aaa | ggt | cgc | tcg | aca | cca | ata | act | tat | tta | ata | aat ggt | 891 |
| Asp | Asp | Asn | Lys | Gly | Arg | Ser | Thr | Pro | Ile | Thr | Tyr | Leu | Ile | Asn Gly |  |
|  |  |  | 240 |  |  |  |  | 245 |  |  |  |  | 250 |  |  |
| tca | tta | gca | cca | aat | gtt | aca | tta | aaa | aat | agc | aac | ata | aaa | ttt taa | 939 |
| Ser | Leu | Ala | Pro | Asn | Val | Thr | Leu | Lys | Asn | Ser | Asn | Ile | Lys | Phe |  |
|  |  | 255 |  |  |  |  | 260 |  |  |  |  | 265 |  |  |  |
| taaataacaa | aaaaggaagg | ttgataaaaa | atg | aca | gta | tat | aac | gca | act ttc | 992 |
|  |  |  | Met | Thr | Val | Tyr | Asn | Ala | Thr Phe |  |
|  |  |  |  | 270 |  |  |  |  | 275 |  |
| acc | att | aat | ttc | tat | aat | gaa | gga | gaa | tgg | ggg | gga | cca | gaa | cca tat | 1040 |
| Thr | Ile | Asn | Phe | Tyr | Asn | Glu | Gly | Glu | Trp | Gly | Gly | Pro | Glu | Pro Tyr |  |
|  |  |  |  | 280 |  |  |  |  | 285 |  |  |  |  | 290 |  |
| ggt | tat | ata | aaa | gca | tat | ctt | aca | aat | cca | gat | cat | gat | ttt | gaa att | 1088 |
| Gly | Tyr | Ile | Lys | Ala | Tyr | Leu | Thr | Asn | Pro | Asp | His | Asp | Phe | Glu Ile |  |
|  |  | 295 |  |  |  |  | 300 |  |  |  |  | 305 |  |  |  |
| tgg | aaa | caa | gat | gat | tgg | ggg | aaa | agt | act | cct | gag | aga | agt | act tat | 1136 |
| Trp | Lys | Gln | Asp | Asp | Trp | Gly | Lys | Ser | Thr | Pro | Glu | Arg | Ser | Thr Tyr |  |
|  | 310 |  |  |  |  | 315 |  |  |  |  | 320 |  |  |  |  |
| acg | caa | acg | att | aaa | ata | agt | agc | gac | act | ggt | tcc | cct | ata | aac caa | 1184 |
| Thr | Gln | Thr | Ile | Lys | Ile | Ser | Ser | Asp | Thr | Gly | Ser | Pro | Ile | Asn Gln |  |
| 325 |  |  |  |  |  | 330 |  |  |  |  | 335 |  |  |  |  |
| atg | tgt | ttt | tat | ggt | gat | gtg | aaa | gaa | tac | gac | gta | gga | aat | gca gat | 1232 |
| Met | Cys | Phe | Tyr | Gly | Asp | Val | Lys | Glu | Tyr | Asp | Val | Gly | Asn | Ala Asp |  |
| 340 |  |  |  | 345 |  |  |  |  | 350 |  |  |  |  | 355 |  |
| gat | att | ctc | gct | tat | cca | agt | caa | aaa | gta | tgc | agt | aca | cct | ggt gta | 1280 |
| Asp | Ile | Leu | Ala | Tyr | Pro | Ser | Gln | Lys | Val | Cys | Ser | Thr | Pro | Gly Val |  |
|  |  |  |  | 360 |  |  |  |  | 365 |  |  |  |  | 370 |  |
| aca | gta | cga | ctt | gat | ggc | gat | gag | aaa | ggt | tct | tat | gtg | aca | att aag | 1328 |
| Thr | Val | Arg | Leu | Asp | Gly | Asp | Glu | Lys | Gly | Ser | Tyr | Val | Thr | Ile Lys |  |
|  |  | 375 |  |  |  |  | 380 |  |  |  |  | 385 |  |  |  |
| tat | tcc | ttg | act | cca | gca | taa | atttcaaata | aatcattgct | taacatattt | 1379 |

-continued

```
Tyr Ser Leu Thr Pro Ala
        390 gaggaccata tctttcctga aatgctagct ctatctttta caaccttcaa tcctcaaaat   1439 tctctaaact agaatcataa aattttatat tctcttatta tgttgcacta ttctaaatgg   1499 ggaatccaac atgctcatct tcaaaaataa taataaaaac tttcaatcta tttagaaatg   1559 caacgaatca ttaatacgca ttatatatag t                                  1590
```

METHODS FOR DETECTING *BACILLUS THURINGIENSIS* CRYET33 AND CRYET34 POLYPEPTIDES

The present application is a division of application Ser. No. 09/949,972, filed Sep. 10, 2001, now U.S. Pat. No. 6,949,626 which is division of application Ser. No. 09/147,992, filed Jul. 21, 1999, now U.S. Pat. No. 6,326,351, which is an §371 national application of PCT/US97/17600, filed Sep. 24, 1997, which a continuation-in-part application based on U.S. patent Ser. No. 08/718,905, filed Sep. 24, 1996, now U.S. Pat. No. 6,063,756. The entire contents of all applications are incorporated herein by reference.

1. BACKGROUND OF THE INVENTION

1.1 Field of the Invention

The present invention relates generally to the fields of molecular biology. More particularly, certain embodiments concern methods and compositions comprising DNA segments, and proteins derived from bacterial species. More particularly, it concerns novel cryET33 and cryET34 genes from *Bacillus thuringiensis* encoding coleopteran-toxic crystal proteins. Various methods for making and using these DNA segments, DNA segments encoding synthetically-modified Cry proteins, and native and synthetic crystal proteins are disclosed, such as, for example, the use of DNA segments as diagnostic probes and templates for protein production, and the use of proteins, fusion protein carriers and peptides in various immunological and diagnostic applications. Also disclosed are methods of making and using nucleic acid segments in the development of transgenic plant cells containing the DNA segments disclosed herein.

1.2 Description of the Related Art

1.2.1 *Bacillus thuringiensis* Crystal Proteins

One of the unique features of *B. thuringiensis* is its production of crystal proteins during sporulation which are specifically toxic to certain orders and species of insects. Many different strains of *B. thuringiensis* have been shown to produce insecticidal crystal proteins. Compositions including *B. thuringiensis* strains which produce proteins having insecticidal activity against lepidopteran and dipteran insects have been commercially available and used as environmentally-acceptable insecticides because they are quite toxic to the specific target insect, but are harmless to plants and other non-targeted organisms.

The mechanism of insecticidal activity of the *B. thuringiensis* crystal proteins has been studied extensively in the past decade. It has been shown that the crystal proteins are toxic to the insect only after ingestion of the protein by the insect. The alkaline pH and proteolytic enzymes in the insect mid-gut solubilize the proteins, thereby allowing the release of components which are toxic to the insect. These toxic components disrupt the mid-gut cells, cause the insect to cease feeding, and, eventually, bring about insect death. For this reason, *B. thuringiensis* has proven to be an effective and environmentally safe insecticide in dealing with various insect pests.

As noted by Höfte et al., (1989) the majority of insecticidal *B. thuringiensis* strains are active against insects of the order Lepidoptera, i.e., caterpillar insects. Other *B. thuringiensis* strains are insecticidally active against insects of the order Diptera, i.e., flies and mosquitoes, or against both lepidopteran and dipteran insects. In recent years, a few *B. thuringiensis* strains have been reported as producing crystal proteins that are toxic to insects of the order Coleoptera, i.e., beetles (Krieg et al., 1983; Sick et al., 1990; Lambert et al., 1992).

1.2.2 Genetics of Crystal Proteins

A number of genes encoding crystal proteins have been cloned from several strains of *B. thuringiensis*. The review by Höfte et al. (1989) discusses the genes and proteins that were identified in *B. thuringiensis* prior to 1990, and sets forth the nomenclature and classification scheme which has traditionally been applied to *B. thuringiensis* genes and proteins. cryI genes encode lepidopteran-toxic CryI proteins. cryII genes encode CryII proteins that are toxic to both lepidopterans and dipterans. cryIII genes encode coleopteran-toxic CryIII proteins, while cryIV genes encode dipteran-toxic CryIV proteins.

Recently a new nomenclature has been proposed which systematically classifies the cry genes based upon DNA sequence homology rather than upon insect specificities. This classification scheme is shown in Table 1.

TABLE 1

REVISED *B. THURINGIENSIS* δ-ENDOTOXIN NOMENCLATURE[A]

| New | Old | GenBank Accession # |
|---|---|---|
| Cry1Aa | CryIA(a) | M11250 |
| Cry1Ab | CryIA(b) | M13898 |
| Cry1Ac | CryIA(c) | M11068 |
| Cry1Ad | CryIA(d) | M73250 |
| Cry1Ae | CryIA(e) | M65252 |
| Cry1Ba | CryIB | X06711 |
| Cry1Bb | ET5 | L32020 |
| Cry1Bc | PEG5 | Z46442 |
| Cry1Bd | CryE1 | U70726 |
| Cry1Ca | CryIC | X07518 |
| Cry1Cb | CryIC(b) | M97880 |
| Cry1Da | CryID | X54160 |
| Cry1Db | PrtB | Z22511 |
| Cry1Ea | CryIE | X53985 |
| Cry1Eb | CryIE(b) | M73253 |
| Cry1Fa | CryIF | M63897 |
| Cry1Fb | PrtD | Z22512 |
| Cry1Ga | PrtA | Z22510 |
| Cry1Gb | CryH2 | U70725 |
| Cry1Ha | PrtC | Z22513 |
| Cry1Hb |  | U35780 |
| Cry1Ia | CryV | X62821 |
| Cry1Ib | CryV | U07642 |
| Cry1Ja | ET4 | L32019 |
| Cry1Jb | ET1 | U31527 |
| Cry1K |  | U28801 |
| Cry2Aa | CryIIA | M31738 |
| Cry2Ab | CryIIB | M23724 |
| Cry2Ac | CryIIC | X57252 |
| Cry3A | CryIIIA | M22472 |
| Cry3Ba | CryIIIB | X17123 |
| Cry3Bb | CryIIIB2 | M89794 |
| Cry3C | CryIIID | X59797 |
| Cry4A | CryIVA | Y00423 |
| Cry4B | CryIVB | X07423 |
| Cry5Aa | CryVA(a) | L07025 |
| Cry5Ab | CryVA(b) | L07026 |
| Cry5B |  | U19725 |
| Cry6A | CryVIA | L07022 |
| Cry6B | CryVIB | L07024 |
| Cry7Aa | CryIIIC | M64478 |
| Cry7Ab | CryIIICb | U04367 |
| Cry8A | CryIIIE | U04364 |
| Cry8B | CryIIIG | U04365 |
| Cry8C | CryIIIF | U04366 |
| Cry9A | CryIG | X58120 |
| Cry9B | CryIX | X75019 |
| Cry9C | CryIH | Z37527 |
| Cry10A | CryIVC | M12662 |
| Cry11A | CryIVD | M31737 |
| Cry11B | Jeg80 | X86902 |
| Cry12A | CryVB | L07027 |
| Cry13A | CryVC | L07023 |

TABLE 1-continued

REVISED *B. THURINGIENSIS* δ-ENDOTOXIN NOMENCLATURE[A]

| New | Old | GenBank Accession # |
|---|---|---|
| Cry14A | CryVD | U13955 |
| Cry15A | 34 kDa | M76442 |
| Cry16A | cbm71 | X94146 |
| Cry17A | cbm71 | X99478 |
| Cry18A | CryBP1 | X99049 |
| Cry19A | Jeg65 | Y08920 |
| Cyt1Aa | CytA | X03182 |
| Cyt1Ab | CytM | X98793 |
| Cyt1B | | U37196 |
| Cyt2A | CytB | Z14147 |
| Cyt2B | CytB | U52043 |

[A]Adapted from Crickmore, N. et al., Microbiol. and Mol. Biol. Rev. (1998) Vol. 62: 8-7-813.

1.2.3 Identification of Crystal Proteins Toxic to Coleopteran Insects

The utility of bacterial crystal proteins as insecticides was extended when the first isolation of a coleopteran-toxic *B. thuringiensis* strain was reported (Kreig et al., 1983; 1984). This strain (described in U.S. Pat. No. 4,766,203, specifically incorporated herein by reference), designated *B. thuringiensis* var. *tenebrionis*, is reported to be toxic to larvae of the coleopteran insects *Agelastica alni* (blue alder leaf beetle) and *Leptinotarsa decemlineata* (Colorado potato beetle).

U.S. Pat. No. 4,766,203 (specifically incorporated herein by reference) relates to a 65-70 kilodalton (kDa) insecticidal crystal protein identified in *B. thuringiensis tenebrionis* (see also Berhnard, 1986). Sekar et al., (1987) report the cloning and characterization of a gene for a coleopteran-toxic crystal protein from *B. thuringiensis tenebrionis*. The predicted size of the polypeptide (as deduced from the gene sequence) is 73 kDa, however, the isolated protein consists primarily of a 65-kDa component. Höfte et al. (1987) also reports the DNA sequence for the cloned gene from *B. thuringiensis tenebrionis*, with the sequence of the gene being identical to that reported by Sekar et al. (1987).

McPherson et al. (1988) discloses a DNA sequence for the cloned insect control gene from *B. thuringiensis tenebrionis*; the sequence was identical to that reported by Sekar et al. (1987). *E. coli* cells and *Pseudomonas fluorescens* cells harboring the cloned gene were found to be toxic to Colorado potato beetle larvae.

Intl. Pat. Appl. Publ. No. WO 91/07481 dated May 30, 1991, describes *B. thuringiensis* mutants that produce high yields of the same insecticidal proteins originally made by the parent strains at lesser yields. Mutants of the coleopteran-toxic *B. thuringiensis tenebrionis* strain are disclosed.

A coleopteran-toxic strain, designated *B. thuringiensis* var. *san diego*, was reported by Herrnstadt et al. (1986) to produce a 64-kDa crystal protein toxic to some coleopterans, including *Pyrrhalta luteola* (elm leaf beetle); *Anthonomus gradis* (boll weevil), *Leptinotarsa decemlineata* (Colorado potato beetle), *Osiorhynchus sulcatus* (black vine weevil), *Tenebrio molitor* (yellow mealworm), *Haltica zombacina*; and *Diabrotica undecimpunctata undecimpunctata* (western spotted cucumber beetle).

The DNA sequence of a coleopteran toxin gene from *B. thuringiensis san diego* was reported by Herrnstadt et al. (1987); and was disclosed in U.S. Pat. No. 4,771,131. The sequence of the toxin gene of *B. thuringiensis san diego* is identical to that reported by Sekar et al. (1987) for the cloned coleopteran toxin gene of *B. thuringiensis tenebrionis*. Krieg et al., (1987) demonstrated that *B. thuringiensis san diego* was identical to *B. thuringiensis tenebrionis*, based on various diagnostic tests.

Another *B. thuringiensis* strain, EG2158, was reported by Donovan et al. (1988) and described in U.S. Pat. No. 5,024, 837. EG2158 produces a 73-kDa CryC crystal protein that is insecticidal to coleopteran insects. Its DNA sequence was identical to that reported by Sekar et al. (1987) for the cloned *B. thuringiensis tenebrionis* toxin gene. This coleopteran toxin gene is referred to as the cryIIIA gene by Höfte et al., 1989. Two minor proteins of 30- and 29-kDa were also observed in this strain, but were not further characterized (Donovan et al., 1988).

U.S. Pat. No. 5,024,837 also describes hybrid *B. thuringiensis* var. *kurstaki* stains which showed activity against both lepidopteran and coleopteran insects. U.S. Pat. No. 4,797,279 (corresponding to EP 0221024) discloses a hybrid *B. thuringiensis* transformed with a plasmid from *B. thuringiensis* var. *kurstaki* containing a lepidopteran-toxic crystal protein-encoding gene and a plasmid from *B. thuringiensis tenebrionis* containing a coleopteran-toxic crystal protein-encoding gene. The hybrid *B. thuringiensis* strain produces crystal proteins characteristic of those made by both *B. thuringiensis kurstaki* and *B. thuringiensis tenebrionis*. U.S. Pat. No. 4,910, 016 (corresponding to EP 0303379) discloses a *B. thuringiensis* isolate identified as *B. thuringiensis* MT 104 which has insecticidal activity against coleopterans and lepidopterans.

European Pat. Appl. Publ. No. 0318143 discloses an intact, partially-modified gene from *B. thuringiensis tenebrionis* and recombinant vectors comprising it able to direct expression of a protein having toxicity to coleopteran insects, and Eur. Pat. Appl. Publ. No. 0324254 discloses *B. thuringiensis* A30; a strain which has insecticidal activity against coleopteran insects, including Colorado potato beetle larvae, corn rootworm larvae and boll weevils.

U.S. Pat. No. 4,999,192 (corresponding to EP 0328383) discloses *B. thuringiensis* PS40D1 which has insecticidal activity against Colorado potato beetle larvae. The strain was also identified via serotyping as being serovar 8a8b, morrisoni. U.S. Pat. No. 5,006,336 (corresponding to EP 0346114) described a *B. thuringiensis* isolate, designated PS122D3, which was serotyped as serovar 8a8b, morrisoni and which exhibited insecticidal activity against Colorado potato beetle larvae. U.S. Pat. No. 4,966,765 (corresponding to EP 0330342) discloses a *B. thuringiensis* strain, PS86B 1 (identified via serotyping as being serovar *tolworthi*), which has insecticidal activity against the Colorado potato beetle.

The nucleotide sequence of a cryIIIB gene and its encoded coleopteran-toxic protein is reported by Sick et al., (1990) but the *B. thuringiensis* source strain is identified only via serotyping as being subspecies *tolworthi*. U.S. Pat. No. 4,966, 155, issued Feb. 26, 1991, of Sick et al. (corresponding to EP 0337604), discloses a *B. thuringiensis* toxin gene obtained from the coleopteran-active *B. thuringiensis* 43F, and the gene sequence appears identical to the cryIIIB gene. *B. thuringiensis* 43F is reported as being active against Colorado potato beetle and *Leptinotarsa texana.*

Eur. Pat. Appl. Publ. No. 0382990 discloses two *B. thuringiensis* strains, btPGS1208 and btPGS1245, which produce crystal proteins of 74- and 129-kDa, respectively, that exhibit insecticidal activity against Colorado potato beetle larvae. The DNA sequence reported for toxin gene producing the 74-kDa protein appears to be related to that of the cryIIIB gene of Sick et al (1990).

PCT Intl. Pat. Appl. Publ. No. WO 90/13651 discloses *B. thuringiensis* strains which contain a toxin gene encoding an 81-kDa protein that is said to be toxic to both lepidopteran and coleopteran insects. U.S. Pat. No. 5,055,293 discloses the use of *B. laterosporous* for corn rootworm (*Diabrotica*) insect control.

2. SUMMARY OF THE INVENTION

In sharp contrast to the prior art, the novel coleopteran-active CryET33 and CryET34 crystal proteins of the present invention and the novel DNA sequences which encode them represent a new class of *B. thuringiensis* crystal proteins, and do not share sequence homology with any of the strains described in the aforementioned literature. The *B. thuringiensis* isolate disclosed and claimed herein represents the first *B. thuringiensis kurstaki* strain that has been shown to be toxic to coleopterans. The *B. thuringiensis* strains of the present invention comprise novel cry genes that express protein toxins having insecticidal activity against coleopterans such as insects of the genera *Popillia* and *Tribolium.*

One aspect of the present invention relates to novel nucleic acid segments that comprise two coleopteran-toxin δ-endotoxin genes having nucleotide base sequences and deduced amino acid sequences as illustrated in FIG. 1A, FIG. 1B, and FIG. 1C. Hereinafter, these genes are designated cryET33 (SEQ ID NO:1) and cryET34 (SEQ ID NO:2). The cryET33 gene has a coding region extending from nucleotide bases 136 to 939 shown in FIG. 1A, FIG. 1B, and FIG. 1C and the cryET34 gene has a coding region extending from nucleotide bases 969 to 1349 shown in FIG. 1A, FIG. 1B, and FIG. 1C.

Another aspect of the present invention relates to the insecticidal proteins encoded by the novel cryET33 and cryET34 genes. The deduced amino acid sequence of the CryET33 protein (SEQ ID NO:3), encoded by the cryET33 gene from the nucleotide bases 136 to 936. is shown in FIG. 1A, FIG. 1B, and FIG. 1C. The deduced amino acid sequence of the CryET34 protein (SEQ ID NO:4), encoded by the cryET34 gene from nucleotide bases 969 to 1346, is also shown in FIG. 1A, FIG. 1B, and FIG. 1C. The proteins exhibit insecticidal activity against insects of the order Coleoptera, in particular, boll weevil, red flour beetle and Japanese beetle.

Another aspect of the present invention relates to a biologically-pure culture of a naturally occurring, wild-type *B. thuringiensis* bacterium, strain EG10327, deposited on Dec. 14, 1994 with the Agricultural Research Culture Collection, Northern Regional Research Laboratory (NRRL) having Accession No. NRRL B-21365. *B. thuringiensis* EG10327 is described infra in sections 5.1-5.3. *B. thuringiensis* EG10327 is a naturally-occurring *B. thuringiensis* strain that contains genes which are related to or identical with the cryET33 and cryET34 genes of the present invention. EG 10327 produces 29-kDa and 14-kDa insecticidal proteins that are related to or identical with the CryET33 and CryET34 proteins disclosed herein.

Another aspect of the present invention relates to a recombinant vector comprising one or both of the novel cryET33 and cryET34 genes, a recombinant host cell transformed with such a recombinant vector, and a biologically pure culture of the recombinant bacterium so transformed. In preferred embodiments, the bacterium preferably being *B. thuringiensis* such as the recombinant strain EG11402 (deposited on Dec. 14, 1994 with the NRRL having Accession No. B-21366) described in Example 8 and the recombinant strain EG11403 (deposited on Dec. 14, 1994 with the NRRL having Accession No. B-21367) described in Example 7. In another preferred embodiment, the bacterium is preferably *E. coli*, such as the recombinant strains EG11460 (deposited on Dec. 14, 1994 with the NRRL having Accession No. B-21364). All strains deposited with the NRRL were deposited in the Patent Culture Collection under the terms of the Budapest Treaty, and viability statements pursuant to International Receipt Form BP/4 were obtained.

2.1 CryET33 and CryET34 DNA Segments

The present invention also concerns DNA segments, that can be isolated from virtually any source, that are free from total genomic DNA and that encode the novel peptides disclosed herein. DNA segments encoding these peptide species may prove to encode proteins, polypeptides, subunits, functional domains, and the like of crystal protein-related or other non-related gene products. In addition these DNA segments may be synthesized entirely in vitro using methods that are well-known to those of skill in the art.

The 1590 nucleotide base region (SEQ ID NO:11) encompassing the cryET33 gene and the cryET34 gene is shown in FIG. 1A, FIG. 1B, and FIG. 1C. The cryET33 gene (SEQ ID NO:1) encodes the 29-kDa CryET33 protein having an amino acid sequence shown in FIG. 1A, FIG. 1B, and FIG. 1C (SEQ ID NO:3). The cryET34 gene (SEQ ID NO:2) encodes the 14-kDa CryET34 protein having an amino acid sequence shown in FIG. 1A, FIG. 1B, and FIG. 1C (SEQ ID NO:4).

As used herein, the term “DNA segment” refers to a DNA molecule that has been isolated free of total genomic DNA of a particular species. Therefore, a DNA segment encoding a crystal protein or peptide refers to a DNA segment that contains crystal protein coding sequences yet is isolated away from, or purified free from, total genomic DNA of the species from which the DNA segment is obtained, which in the instant case is the genome of the Gram-positive bacterial genus, *Bacillus*, and in particular, the species of *Bacillus* known as *B. thuringiensis*. Included within the term “DNA segment”, are DNA segments and smaller fragments of such segments, and also recombinant vectors, including, for example, plasmids, cosmids, phagemids, phage, viruses, and the like.

Similarly, a DNA segment comprising an isolated or purified crystal protein-encoding gene refers to a DNA segment which may include in addition to peptide encoding sequences, certain other elements such as, regulatory sequences, isolated substantially away from other naturally occurring genes or protein-encoding sequences. In this respect, the term “gene” is used for simplicity to refer to a functional protein-, polypeptide- or peptide-encoding unit. As will be understood by those in the art, this functional term includes both genomic sequences, operon sequences and smaller engineered gene segments that express, or may be adapted to express, proteins, polypeptides or peptides.

“Isolated substantially away from other coding sequences” means that the gene of interest, in this case, a gene encoding a bacterial crystal protein, forms the significant part of the coding region of the DNA segment, and that the DNA segment does not contain large portions of naturally-occurring coding DNA, such as large chromosomal fragments or other functional genes or operon coding regions. Of course, this refers to the DNA segment as originally isolated, and does not exclude genes, recombinant genes, synthetic linkers, or coding regions later added to the segment by the hand of man.

In particular embodiments, the invention concerns isolated DNA segments and recombinant vectors incorporating DNA sequences that encode a Cry peptide species that includes within its amino acid sequence an amino acid sequence essentially as set forth in SEQ ID NO:3 or SEQ ID NO:4.

The term “a sequence essentially as set forth in SEQ ID NO:3 or SEQ ID NO:4,” means that the sequence substantially corresponds to a portion of the sequence of either SEQ ID NO:3 or SEQ ID NO:4 and has relatively few amino acids that are not identical to, or a biologically functional equivalent of, the amino acids of any of these sequences. The term "biologically functional equivalent" is well understood in the art and is further defined in detail herein (e.g., see Illustrative Embodiments). Accordingly, sequences that have between about 70% and about 80%, or more preferably between about 81% and about 90%, or even more preferably between about 91% and about 99% amino acid sequence identity or functional equivalence to the amino acids of SEQ ID NO:3 or SEQ ID NO:4 will be sequences that are "essentially as set forth in SEQ ID NO:3 or SEQ ID NO:4."

It will also be understood that amino acid and nucleic acid sequences may include additional residues, such as additional N— or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch encoding either of the peptide sequences disclosed in SEQ ID NO:3 or SEQ ID NO:4, or that are identical to or complementary to DNA sequences which encode any of the peptides disclosed in SEQ ID NO:3 or SEQ ID NO:4, and particularly those DNA segments disclosed in SEQ ID NO:1 or SEQ ID NO:2. For example, DNA sequences such as about 18 nucleotides, and that are up to about 10,000, about 5,000, about 3,000, about 2,000, about 1,000, about 500, about 200, about 100, about 50, and about 14 base pairs in length (including all intermediate lengths) are also contemplated to be useful.

It will be readily understood that "intermediate lengths", in these contexts, means any length between the quoted ranges, such as 18, 19, 20, 21, 22, 23, etc.; 30, 31, 32, etc.; 50, 51, 52, 53, etc.; 100, 101, 102, 103, etc.; 150, 151, 152, 153, etc.; including all integers through the 200-500; 500-1,000; 1,000-2,000; 2,000-3,000; 3,000-5,000; and up to and including sequences of about 5200 nucleotides and the like.

It will also be understood that this invention is not limited to the particular nucleic acid sequences which encode peptides of the present invention, or which encode the amino acid sequences of SEQ ID NO:3 or SEQ ID NO:4, including those DNA sequences which are particularly disclosed in SEQ ID NO:1 or SEQ ID NO:2. Recombinant vectors and isolated DNA segments may therefore variously include the peptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA segments of the present invention encompass biologically-functional, equivalent peptides. Such sequences may arise as a consequence of codon degeneracy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

If desired, one may also prepare fusion proteins and peptides, e.g., where the peptide-coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full length protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning and/or PCR™ technology, in connection with the compositions disclosed herein.

2.2 CryET33 and CryET34 DNA Segments as Hybridization Probes and Primers

In addition to their use in directing the expression of crystal proteins or peptides of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous DNA segment of SEQ ID NO:1 or SEQ ID NO:2 will find particular utility. Longer contiguous identical or complementary sequences, e.g., those of about 20, 30, 40, 50, 100, 200, 500, 1000, 2000, 5000 bp, etc. (including all intermediate lengths and up to and including the full-length sequence of 5200 basepairs will also be of use in certain embodiments.

The ability of such nucleic acid probes to specifically hybridize to crystal protein-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10-14, 15-20, 30, 50, or even of 100-200 nucleotides or so, identical or complementary to DNA sequences of SEQ ID NO:1 or SEQ ID NO:2, are particularly contemplated as hybridization probes for use in, e.g., Southern and Northern blotting. Smaller fragments will generally find use in hybridization embodiments, wherein the length of the contiguous complementary region may be varied, such as between about 10-14 and about 100 or 200 nucleotides, but larger contiguous complementary stretches may be used, according to the length complementary sequences one wishes to detect.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating crystal protein-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1993; Segal 1976; Prokop, 1991; and Kuby, 1991, are particularly relevant.

Of course, for some applications, for example, where one desires to prepare mutants employing a mutant primer strand hybridized to an underlying template or where one seeks to isolate crystal protein-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmentally undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

2.3 Recombinant Vectors and Crystal Protein Expression

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding a crystal protein or peptide in its natural environment. Such promoters may include promoters normally associated with other genes, and/or promoters isolated from any bacterial, viral, eukaryotic, or plant cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the Pichia expression vector system (Pharmacia LKB Biotechnology).

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of crystal peptides or epitopic core regions, such as may be used to generate anti-crystal protein antibodies, also falls within the scope of the invention. DNA segments that encode peptide antigens from about 8 to about 50 amino acids in length, or more preferably, from about 8 to about 30 amino acids in length, or even more preferably, from about 8 to about 20 amino acids in length are contemplated to be particularly useful. Such peptide epitopes may be amino acid sequences which comprise contiguous amino acid sequences from SEQ ID NO:3 or SEQ ID NO:4.

2.4 Crystal Protein Transgenes and Transgenic Plants

In yet another aspect, the present invention provides methods for producing a transgenic plant which expresses a nucleic acid segment encoding the novel crystal protein of the present invention. The process of producing transgenic plants is well-known in the art. In general, the method comprises transforming a suitable host cell with a DNA segment which contains a promoter operatively linked to a coding region that encodes a *B. thuringiensis* CryET33 or CryET34 crystal protein. Such a coding region is generally operatively linked to a transcription-terminating region, whereby the promoter is capable of driving the transcription of the coding region in the cell, and hence providing the cell the ability to produce the recombinant protein in vivo. Alternatively, in instances where it is desirable to control, regulate, or decrease the amount of a particular recombinant crystal protein expressed in a particular transgenic cell, the invention also provides for the expression of crystal protein antisense mRNA. The use of antisense mRNA as a means of controlling or decreasing the amount of a given protein of interest in a cell is well-known in the art.

Another aspect of the invention comprises transgenic plants which express a gene or gene segment encoding one or more of the novel polypeptide compositions disclosed herein. As used herein, the term "transgenic plant" is intended to refer to a plant that has incorporated DNA sequences, including but not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression.

It is contemplated that in some instances the genome of a transgenic plant of the present invention will have been augmented through the stable introduction of one or more cryET33 or cryET34 transgenes, either native, synthetically modified, or mutated. In some instances, more than one transgene will be incorporated into the genome of the transformed host plant cell. Such is the case when more than one crystal protein-encoding DNA segment is incorporated into the genome of such a plant. In certain situations, it may be desirable to have one, two, three, four, or even more *B. thuringiensis* crystal proteins (either native or recombinantly-engineered) incorporated and stably expressed in the transformed transgenic plant.

A preferred gene which may be introduced includes, for example, a crystal protein-encoding DNA sequence from bacterial origin, and particularly one or more of those described herein which are obtained from *Bacillus* spp. Highly preferred nucleic acid sequences are those obtained from *B. thuringiensis*, or any of those sequences which have been genetically engineered to decrease or increase the insecticidal activity of the crystal protein in such a transformed host cell.

Means for transforming a plant cell and the preparation of a transgenic cell line are well-known in the art, and are discussed herein. Vectors, plasmids, cosmids, YACs (yeast artificial chromosomes) and DNA segments for use in transforming such cells will, of course, generally comprise either the operons, genes, or gene-derived sequences of the present invention, either native, or synthetically-derived, and particularly those encoding the disclosed crystal proteins. These DNA constructs can further include structures such as promoters, enhancers, polylinkers, or even gene sequences which have positively- or negatively-regulating activity upon the particular genes of interest as desired. The DNA segment or gene may encode either a native or modified crystal protein, which will be expressed in the resultant recombinant cells, and/or which will impart an improved phenotype to the regenerated plant.

Such transgenic plants may be desirable for increasing the insecticidal resistance of a monocotyledonous or dicotyledonous plant, by incorporating into such a plant, a transgenic DNA segment encoding one or more CryET33 and/or CryET34 crystal proteins which is toxic to Coleopteran insects. Particularly preferred plants include turf grasses, wheat, vegetables, ornamental plants, fruit trees, and the like.

In a related aspect, the present invention also encompasses a seed produced by the transformed plant, a progeny from such seed, and a seed produced by the progeny of the original transgenic plant, produced in accordance with the above process. Such progeny and seeds will have a crystal protein-encoding transgene stably incorporated into their genome, and such progeny plants will inherit the traits afforded by the introduction of a stable transgene in Mendelian fashion. All such transgenic plants having incorporated into their genome transgenic DNA segments encoding one or more CryET33 and/or CryET34 crystal proteins or polypeptides are aspects of this invention.

2.5 Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 13 or about 14 or about 16 or about 17 up to and including about 18 or about 19 or about 20, or about 21, 22, 23, 24, 25 26, 27, 28, 29 or even about 30, 40, or about 50 or so nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

2.6 CryET33 and CryET34 Antibody Compositions and Methods of Making

In particular embodiments, the inventors contemplate the use of antibodies, either monoclonal or polyclonal which bind to the crystal proteins disclosed herein. Means for preparing and characterizing antibodies are well known in the art (See, e.g., Antibodies: A Laboratory Manual, Cold Spring Harbor Laboratory, 1988; incorporated herein by reference). The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified crystal protein, polypeptide or peptide. The immunizing composition is administered in a manner effective to stimulate antibody producing cells. Rodents such as mice and rats are preferred animals, however, the use of rabbit, sheep, or frog cells is also possible. The use of rats may provide certain advantages (Goding, 1986, pp. 60-61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render them incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, (Gefter et al., 1977). The use of electrically induced fusion methods is also appropriate (Goding, 1986, pp. 71-74).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

2.7 ELISAs and Immunoprecipitation

ELISAs may be used in conjunction with the invention. In an ELISA assay, proteins or peptides incorporating crystal protein antigen sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hours, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

Following formation of specific immunocomplexes between the test sample and the bound antigen, and subsequent washing, the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hours at room temperature in a PBS-containing solution such as PBS Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectra spectrophotometer.

The anti-crystal protein antibodies of the present invention are particularly useful for the isolation of other crystal protein antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g. enzyme-substrate pairs.

2.8 Western Blots

The compositions of the present invention will find great use in immunoblot or western blot analysis. The anti-peptide antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the toxin moiety are considered to be of particular use in this regard.

2.9 Crystal Protein Screening and Detection Kits

The present invention contemplates methods and kits for screening samples suspected of containing crystal protein polypeptides or crystal protein-related polypeptides, or cells producing such polypeptides. A kit may contain one or more antibodies of the present invention, and may also contain reagent(s) for detecting an interaction between a sample and an antibody of the present invention. The provided reagent(s) can be radio-, fluorescently- or enzymatically-labeled. The kit can contain a known radiolabeled agent capable of binding or interacting with a nucleic acid or antibody of the present invention.

The reagent(s) of the kit can be provided as a liquid solution, attached to a solid support or as a dried powder. Preferably, when the reagent(s) are provided in a liquid solution, the liquid solution is an aqueous solution. Preferably, when the reagent(s) provided are attached to a solid support, the solid support can be chromatograph media, a test plate having a plurality of wells, or a microscope slide. When the reagent(s) provided are a dry powder, the powder can be reconstituted by the addition of a suitable solvent, that may be provided.

In still further embodiments, the present invention concerns immunodetection methods and associated kits. It is proposed that the crystal proteins or peptides of the present invention may be employed to detect antibodies having reactivity therewith, or, alternatively, antibodies prepared in accordance with the present invention, may be employed to detect crystal proteins or crystal protein-related epitope-containing peptides. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For assaying purposes, it is proposed that virtually any sample suspected of comprising either a crystal protein or peptide or a crystal protein-related peptide or antibody sought to be detected, as the case may be, may be employed. It is contemplated that such embodiments may have application in the titering of antigen or antibody samples, in the selection of hybridomas, and the like. In related embodiments, the present invention contemplates the preparation of kits that may be employed to detect the presence of crystal proteins or related peptides and/or antibodies in a sample. Samples may include cells, cell supernatants, cell suspensions, cell extracts, enzyme fractions, protein extracts, or other cell-free compositions suspected of containing crystal proteins or peptides. Generally speaking, kits in accordance with the present invention will include a suitable crystal protein, peptide or an antibody directed against such a protein or peptide, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

2.10 Epitopic Core Sequences

The present invention is also directed to protein or peptide compositions, free from total cells and other peptides, which comprise a purified protein or peptide which incorporates an epitope that is immunologically cross-reactive with one or more anti-crystal protein antibodies. In particular, the invention concerns epitopic core sequences derived from Cry proteins or peptides.

As used herein, the term "incorporating an epitope(s) that is immunologically cross-reactive with one or more anti-crystal protein antibodies" is intended to refer to a peptide or protein antigen which includes a primary, secondary or tertiary structure similar to an epitope located within a crystal protein or polypeptide. The level of similarity will generally be to such a degree that monoclonal or polyclonal antibodies directed against the crystal protein or polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of Cry immunodominant epitopes, and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 8 to about 20 amino acids in length, and more preferably about 8 to about 15 amino acids in length. It is proposed that shorter antigenic crystal protein-derived peptides will provide advantages in certain circumstances, for example, in the preparation of immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to crystal proteins, and in particular Cry and Cry-related sequences. These epitopic core sequences are identified herein in particular aspects as hydrophilic regions of the particular polypeptide antigen. It is proposed that these regions represent those which are most likely to promote T-cell or B-cell stimulation, and, hence, elicit specific antibody production.

An epitopic core sequence, as used herein, is a relatively short stretch of amino acids that is "complementary" to, and therefore will bind, antigen binding sites on the crystal protein-directed antibodies disclosed herein. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence expected by the present disclosure would generally be on the order of about 8 amino acids in length, with sequences on the order of 10 to 20 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g., DNAStar® software, DNAStar, Inc., Madison, Wis.) may also be useful in designing synthetic peptides in accordance with the present disclosure.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquotted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at about 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

2.11 Biological Functional Equivalents

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. In particular embodiments of the invention, mutated crystal proteins are contemplated to be useful for increasing the insecticidal activity of the protein, and consequently increasing the insecticidal activity and/or expression of the recombinant transgene in a plant cell. The amino acid changes may be achieved by changing the codons of the DNA sequence, according to the codons given in Table 2.

TABLE 2

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

2.12 Crystal Protein Composition as Insecticides and Methods of Use

The inventors contemplate that the crystal protein compositions disclosed herein will find particular utility as insecticides for topical and/or systemic application to field crops, grasses, fruits and vegetables, and ornamental plants. In a preferred embodiment, the bioinsecticide composition comprises an oil flowable suspension of bacterial cells which expresses a novel crystal protein disclosed herein. Preferably the cells are *B. thuringiensis* EG10327 cells, however, any such bacterial host cell expressing the novel nucleic acid segments disclosed herein and producing a crystal protein is contemplated to be useful, such as *B. thuringiensis, B. megaterium, B. subtilis, E. coli,* or *Pseudomonas* spp.

In another important embodiment, the bioinsecticide composition comprises a water dispersible granule. This granule comprises bacterial cells which expresses a novel crystal protein disclosed herein. Preferred bacterial cells are *B. thuringiensis* EG10327 cells, however, bacteria such as *B. thuringiensis, B. megaterium, B. subtilis, E. coli,* or *Pseudomonas* spp. cells transformed with a DNA segment disclosed herein and expressing the crystal protein are also contemplated to be useful.

In a third important embodiment, the bioinsecticide composition comprises a wettable powder, dust, pellet, or collodial concentrate. This powder comprises bacterial cells which expresses a novel crystal protein disclosed herein. Preferred bacterial cells are *B. thuringiensis* EG10327 cells, however, bacteria such as *B. thuringiensis, B. megaterium, B. subtilis, E. coli,* or *Pseudomonas* spp. cells transformed with a DNA segment disclosed herein and expressing the crystal protein are also contemplated to be useful. Such dry forms of the insecticidal compositions may be formulated to dissolve immediately upon wetting, or alternatively, dissolve in a controlled-release, sustained-release, or other time-dependent manner.

In a fourth important embodiment, the bioinsecticide composition comprises an aqueous suspension of bacterial cells such as those described above which express the crystal protein. Such aqueous suspensions may be provided as a concentrated stock solution which is diluted prior to application, or alternatively, as a diluted solution ready-to-apply.

For these methods involving application of bacterial cells, the cellular host containing the crystal protein gene(s) may be grown in any convenient nutrient medium, where the DNA construct provides a selective advantage, providing for a selective medium so that substantially all or all of the cells retain the *B. thuringiensis* gene. These cells may then be harvested in accordance with conventional ways. Alternatively, the cells can be treated prior to harvesting.

When the insecticidal compositions comprise intact *B. thuringiensis* cells expressing the protein of interest, such bacteria may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, suspensions, emulsifiable concentrates, or the like. The ingredients may include rheological agents, surfactants, emulsifiers, dispersants, or polymers.

Alternatively, the novel CryET33 and/or CryET34 proteins may be prepared by native or recombinant bacterial expression systems in vitro and isolated for subsequent field application. Such protein may be either in crude cell lysates, suspensions, colloids, etc., or alternatively may be purified, refined, buffered, and/or further processed, before formulating in an active biocidal formulation. Likewise, under certain circumstances, it may be desirable to isolate crystals and/or spores from bacterial cultures expressing the crystal protein and apply solutions, suspensions, or collodial preparations of such crystals and/or spores as the active bioinsecticidal composition.

Regardless of the method of application, the amount of the active component(s) is applied at an insecticidally-effective amount, which will vary depending on such factors as, for example, the specific coleopteran insects to be controlled, the specific plant or crop to be treated, the environmental conditions, and the method, rate, and quantity of application of the insecticidally-active composition.

The insecticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, dessicated, or in an aqueous carrier, medium or suitable diluent, such as saline or other buffer.

The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, e.g., inert components, dispersants, surfactants, tackifiers, binders, etc. that are ordinarily used in insecticide formulation technology; these are well known to those skilled in insecticide formulation. The formulations may be mixed with one or more solid or liquid adjuvants and prepared by various means, e.g., by homogeneously mixing, blending and/or grinding the insecticidal composition with suitable adjuvants using conventional formulation techniques.

The insecticidal compositions of this invention are applied to the environment of the target coleopteran insect, typically onto the foliage of the plant or crop to be protected, by conventional methods, preferably by spraying. The strength and duration of insecticidal application will be set with regard to conditions specific to the particular pest(s), crop(s) to be treated and particular environmental conditions. The proportional ratio of active ingredient to carrier will naturally depend on the chemical nature, solubility, and stability of the insecticidal composition, as well as the particular formulation contemplated.

Other application techniques, e.g., dusting, sprinkling, soaking, soil injection, seed coating, seedling coating, spraying, aerating, misting, atomizing, and the like, are also feasible and may be required under certain circumstances such as e.g., insects that cause root or stalk infestation, or for application to delicate vegetation or ornamental plants. These application procedures are also well-known to those of skill in the art.

The insecticidal composition of the invention may be employed in the method of the invention singly or in combination with other compounds, including and not limited to other pesticides. The method of the invention may also be used in conjunction with other treatments such as surfactants, detergents, polymers or time-release formulations. The insecticidal compositions of the present invention may be formulated for either systemic or topical use.

The concentration of insecticidal composition which is used for environmental, systemic, or foliar application will vary widely depending upon the nature of the particular formulation, means of application, environmental conditions, and degree of biocidal activity. Typically, the bioinsecticidal composition will be present in the applied formulation at a concentration of at least about 1% by weight and may be up to and including about 99% by weight. Dry formulations of the compositions may be from about 1% to about 99% or more by weight of the composition, while liquid formulations may generally comprise from about 1% to about 99% or more of the active ingredient by weight. Formulations which comprise intact bacterial cells will generally contain from about $10^4$ to about $10^7$ cells/mg.

The insecticidal formulation may be administered to a particular plant or target area in one or more applications as needed, with a typical field application rate per hectare ranging on the order of from about 50 g to about 500 g of active ingredient, or of from about 500 g to about 1000 g, or of from about 1000 g to about 5000 g or more of active ingredient.

3. BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 1A, FIG. 1B, and FIG. 1C show the 1590 nucleotide base region (SEQ ID NO:11) encompassing the cryET33 gene and the cryET34 gene, as well as the deduced amino acid sequences of the CryET33 protein (SEQ ID NO:3) and the CryET34 protein (SEQ ID NO:4).

FIG. 2 shows a restriction map of pEG246. The locations and orientations of the cryET33 gene (SEQ ID NO:1) and the cryET34 gene (SEQ ID NO:2) are indicated by arrows. pEG246 is functional in *E. coli* since it is derived from pBR322, and is ampicillin resistant ($Amp^R$). The abbreviations for the restriction endonuclease cleavage sites are as follows: R=EcoR1, B=BamHI. Also shown in FIG. 2 is a one kilobase (1 kb) size marker.

Figure 3:
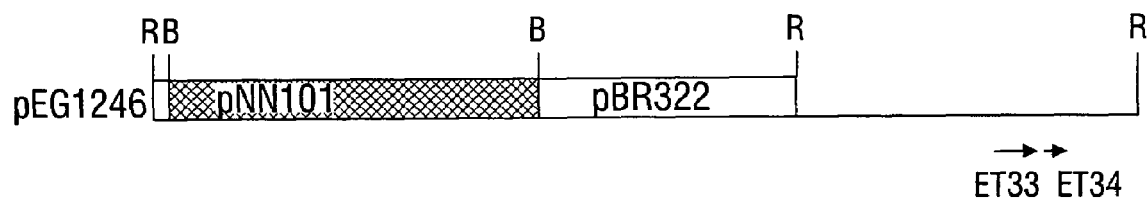

FIG. 3, aligned with and based on the same scale as FIG. 2, shows a restriction map of pEG 1246. The locations and orientations of the cryET33 gene (SEQ ID NO: 1) and the cryET34 gene (SEQ ID NO:2) are indicated by arrows. pEG1246 is derived from plasmid pEG246 (FIG. 2) and contains the Bacillus spp. plasmid, pNN101 (which expresses both chloramphenicol resistance [$Cam^R$] and tetracycline resistance [$Tet^R$]) inserted into the BamHI site of pEG246. pEG 1246 is functional in both *E. coli* and *B. thuringiensis*. Abbreviations are the same as those for FIG. 2.

4. DESCRIPTION OF ILLUSTRATIVE EMBODIMENTS

4.1 Some Advantages of the Invention

*B. thuringiensis* EG10327 is a naturally-occurring strain that exhibits insecticidal activity against coleopteran insects including boll weevil, red flour beetle larvae (*Tribolium castaneum*) and Japanese beetle larvae (*Popillia japonica*). *B. thuringiensis* EG2158 contains colepteran-toxic crystal protein genes similar to, or identical with, the crystal protein genes of EG10327. Two novel crystal toxin genes, designated cryET33 and cryET34, were cloned from EG2158. The cryET33 gene encodes the 29-kDa CryET33 crystal protein, and the cryET34 gene encodes the 14-kDa CryET34 crystal protein. The CryET33 and CryET34 crystal proteins are toxic to red flour beetle larvae, boll weevil larvae, and Japanese beetle larvae.

4.2 Definitions

The following words and phrases have the meanings set forth below.

Expression: The combination of intracellular processes, including transcription and translation undergone by a coding DNA molecule such as a structural gene to produce a polypeptide.

Promoter: A recognition site on a DNA sequence or group of DNA sequences that provide an expression control element for a structural gene and to which RNA polymerase specifically binds and initiates RNA synthesis (transcription) of that gene.

Regeneration: The process of growing a plant from a plant cell (e.g., plant protoplast or explant).

Structural gene: A gene that is expressed to produce a polypeptide.

Transformation: A process of introducing an exogenous DNA sequence (e.g., a vector, a recombinant DNA molecule) into a cell or protoplast in which that exogenous DNA is incorporated into a chromosome or is capable of autonomous replication.

Transformed cell: A cell whose DNA has been altered by the introduction of an exogenous DNA molecule into that cell.

Transgenic cell: Any cell derived or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant.

Transgenic plant: A plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

Vector: A DNA molecule capable of replication in a host cell and/or to which another DNA segment can be operatively linked so as to bring about replication of the attached segment. A plasmid is an exemplary vector.

4.3 Probes and Primers

In another aspect, DNA sequence information provided by the invention allows for the preparation of relatively short DNA (or RNA) sequences having the ability to specifically hybridize to gene sequences of the selected polynucleotides disclosed herein. In these aspects, nucleic acid probes of an appropriate length are prepared based on a consideration of a selected crystal protein gene sequence, e.g., a sequence such as that shown in SEQ ID NO:1 or SEQ ID NO:2. The ability of such DNAs and nucleic acid probes to specifically hybridize to a crystal protein-encoding gene sequence lends them particular utility in a variety of embodiments. Most importantly, the probes may be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a crystal protein gene from *B. thuringiensis* using PCR™ technology. Segments of related crystal protein genes from other species may also be amplified by PCR™ using such primers.

To provide certain of the advantages in accordance with the present invention, a preferred nucleic acid sequence employed for hybridization studies or assays includes sequences that are complementary to at least a 14 to 30 or so long nucleotide stretch of a crystal protein-encoding sequence, such as that shown in SEQ ID NO:1 or SEQ ID NO:2. A size of at least 14 nucleotides in length helps to ensure that the fragment will be of sufficient length to form a duplex molecule that is both stable and selective. Molecules having complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired. Such fragments may be readily prepared by, for example, directly synthesizing the fragment by chemical means, by application of nucleic acid reproduction technology, such as the PCR™ technology of U.S. Pat. Nos. 4,683,195, and 4,683,202, herein incorporated by reference, or by excising selected DNA fragments from recombinant plasmids containing appropriate inserts and suitable restriction sites.

4.4 Expression Vectors

The present invention contemplates an expression vector comprising a polynucleotide of the present invention. Thus, in one embodiment an expression vector is an isolated and purified DNA molecule comprising a promoter operatively linked to an coding region that encodes a polypeptide of the present invention, which coding region is operatively linked to a transcription-terminating region, whereby the promoter drives the transcription of the coding region.

As used herein, the term "operatively linked" means that a promoter is connected to an coding region in such a way that the transcription of that coding region is controlled and regulated by that promoter. Means for operatively linking a promoter to a coding region are well known in the art.

In a preferred embodiment, the recombinant expression of DNAs encoding the crystal proteins of the present invention is preferable in a Bacillus host cell. Preferred host cells include *B. thuringiensis, B. megaterium, B. subtilis*, and related bacilli, with *B. thuringiensis* host cells being highly preferred. Promoters that function in bacteria are well-known in the art. An exemplary and preferred promoter for the *Bacillus* crystal proteins include any of the known crystal protein gene promoters, including the cryET33 and cryET34 gene promoters. Alternatively, mutagenized or recombinant crystal protein-encoding gene promoters may be engineered by the hand of man and used to promote expression of the novel gene segments disclosed herein.

In an alternate embodiment, the recombinant expression of DNAs encoding the crystal proteins of the present invention is performed using a transformed Gram-negative bacterium such as an *E. coli* or *Pseudomonas* spp. host cell. Promoters which function in high-level expression of target polypeptides in *E. coli* and other Gram-negative host cells are also well-known in the art.

Where an expression vector of the present invention is to be used to transform a plant, a promoter is selected that has the ability to drive expression in plants. Promoters that function in plants are also well known in the art. Useful in expressing the polypeptide in plants are promoters that are inducible, viral, synthetic, constitutive as described (Poszkowski et al., 1989; Odell et al., 1985), and temporally regulated, spatially regulated, and spatio-temporally regulated (Chau et al., 1989).

A promoter is also selected for its ability to direct the transformed plant cell's or transgenic plant's transcriptional activity to the coding region. Structural genes can be driven by a variety of promoters in plant tissues. Promoters can be near-constitutive, such as the CaMV 35S promoter, or tissue-specific or developmentally specific promoters affecting dicots or monocots.

Where the promoter is a near-constitutive promoter such as CaMV 35S, increases in polypeptide expression are found in a variety of transformed plant tissues (e.g., callus, leaf, seed and root). Alternatively, the effects of transformation can be directed to specific plant tissues by using plant integrating vectors containing a tissue-specific promoter.

An exemplary tissue-specific promoter is the lectin promoter, which is specific for seed tissue. The Lectin protein in soybean seeds is encoded by a single gene (Le1) that is only expressed during seed maturation and accounts for about 2 to about 5% of total seed mRNA. The lectin gene and seed-specific promoter have been fully characterized and used to direct seed specific expression in transgenic tobacco plants (Vodkin et al., 1983; Lindstrom et al., 1990.)

An expression vector containing a coding region that encodes a polypeptide of interest is engineered to be under control of the lectin promoter and that vector is introduced into plants using, for example, a protoplast transformation method (Dhir et al., 1991). The expression of the polypeptide is directed specifically to the seeds of the transgenic plant.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

Exemplary tissue-specific promoters are corn sucrose synthetase 1 (Yang et al., 1990), corn alcohol dehydrogenase 1 (Vogel et al., 1989), corn light harvesting complex (Simpson, 1986), corn heat shock protein (Odell et al., 1985), pea small subunit RuBP carboxylase (Poulsen et al., 1986; Cashmore et al., 1983), Ti plasmid mannopine synthase (Langridge et al., 1989), Ti plasmid nopaline synthase (Langridge et al., 1989), petunia chalcone isomerase (Van Tunen et al., 1988), bean glycine rich protein 1 (Keller et al., 1989), CaMV 35s transcript (Odell et al., 1985) and Potato patatin (Wenzler et al., 1989). Preferred promoters are the cauliflower mosaic virus (CaMV 35S) promoter and the S-E9 small subunit RuBP carboxylase promoter.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors useful for expression of genes in higher plants are well known in the art and include vectors derived from the tumor-inducing (Ti) plasmid of *Agrobacterium tumefaciens* described (Rogers et al., 1987). However, several other plant integrating vector systems are known to function in plants including pCaMVCN transfer control vector described (Fromm et al., 1985). Plasmid pCaMVCN (available from Pharmacia, Piscataway, N.J.) includes the cauliflower mosaic virus CaMV 35S promoter.

In preferred embodiments, the vector used to express the polypeptide includes a selection marker that is effective in a plant cell, preferably a drug resistance selection marker. One preferred drug resistance marker is the gene whose expression results in kanamycin resistance; i.e., the chimeric gene containing the nopaline synthase promoter, Tn5 neomycin phosphotransferase II (nptII) and nopaline synthase 3' non-translated region described (Rogers et al., 1988).

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Means for preparing expression vectors are well known in the art. Expression (transformation vectors) used to transform plants and methods of making those vectors are described in U.S. Pat. Nos. 4,971,908, 4,940,835, 4,769,061 and 4,757,011, the disclosures of which are incorporated herein by reference. Those vectors can be modified to include a coding sequence in accordance with the present invention.

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

A coding region that encodes a polypeptide having the ability to confer insecticidal activity to a cell is preferably a CryET33 or CryET34 B. thuringiensis crystal protein-encoding gene. In preferred embodiments, such a polypeptide has the amino acid residue sequence of SEQ ID NO:3 or SEQ ID NO:4, or a functional equivalent of those sequences. In accordance with such embodiments, a coding region comprising the DNA sequence of SEQ ID NO:1 or the DNA sequence of SEQ ID NO:2 is also preferred

4.5 Characteristics of the Novel Crystal Proteins

The present invention provides novel polypeptides that define a whole or a portion of a *B. thuringiensis* CryET33 or CryET34 crystal protein.

In a preferred embodiment, the invention discloses and claims an isolated and purified CryET33 protein. The CryET33 protein comprises a 267-amino acid sequence, and has a calculated molecular mass of 29,216 Da. CryET33 has a calculated isoelectric constant (pI) equal to 4.78. The amino acid composition of the CryET33 protein is given in Table 3.

TABLE 3

AMINO ACID COMPOSITION OF CRYET33

| Amino Acid | # Residues | % Total |
|---|---|---|
| Ala | 14 | (5.2) |
| Arg | 5 | (1.9) |
| Asn | 22 | (8.2) |
| Asp | 12 | (4.5) |
| Cys | 2 | (0.7) |
| Gln | 7 | (2.6) |
| Glu | 15 | (5.6) |
| Gly | 18 | (6.7) |
| His | 3 | (1.1) |
| Ile | 17 | (6.3) |
| Leu | 12 | (4.5) |
| Lys | 14 | (5.2) |
| Met | 3 | (1.1) |
| Phe | 11 | (4.1) |
| Pro | 12 | (4.5) |
| Ser | 22 | (8.2) |
| Thr | 39 | (14.5) |
| Trp | 2 | (0.7) |
| Tyr | 14 | (5.2) |
| Val | 23 | (8.6) |
| Acidic (Asp + Glu) | 27 | (10.0) |
| Basic (Arg + Lys) | 19 | (7.1) |
| Aromatic (Phe + Trp + Tyr) | 27 | (10.0) |
| Hydrophobic (Aromatic + Ile + Leu + Met + Val) | 82 | (30.5) |

In another embodiment, the invention discloses and claims an isolated and purified CryET34 protein. The CryET34 protein comprises a 126-amino acid sequence and has a calculated molecular mass of 14,182 Da. The calculated isoelectric point (pI) of CryET34 is 4.26. The amino acid composition of the CryET34 protein is given in Table 4.

TABLE 4

AMINO ACID COMPOSITION OF CRYET34

| Amino Acid | # Residues | % Total |
|---|---|---|
| Ala | 5 | (3.9) |
| Arg | 2 | (1.6) |
| Asn | 6 | (4.7) |
| Asp | 11 | (8.7) |
| Cys | 2 | (1.6) |
| Gln | 4 | (3.1) |
| Glu | 7 | (5.5) |
| Gly | 11 | (8.7) |
| His | 1 | (0.8) |
| Ile | 8 | (6.3) |
| Leu | 4 | (3.1) |
| Lys | 8 | (6.3) |
| Met | 2 | (1.6) |
| Phe | 4 | (3.1) |
| Pro | 8 | (6.3) |
| Ser | 9 | (7.1) |
| Thr | 13 | (10.2) |
| Trp | 3 | (2.4) |
| Tyr | 11 | (8.7) |
| Val | 7 | (5.5) |
| Acidic (Asp + Glu) | 18 | (14.2) |
| Basic (Arg + Lys) | 10 | (7.9) |
| Aromatic (Phe + Trp + Tyr) | 18 | (14.2) |
| Hydrophobic (Aromatic + Ile + Leu + Met + Val) | 39 | (30.7) |

4.6 Nomenclature of the Novel Proteins

The inventors have arbitrarily assigned the designations CryET33 and CryET34 to the novel proteins of the invention. Likewise, the arbitrary designations of cryET33 and cryET34 have been assigned to the novel nucleic acid sequences which encode these polypeptides, respectively. Formal assignment of gene and protein designations based on the revised nomenclature of crystal protein endotoxins (Table 1) will be assigned by a committee on the nomenclature of *B. thuringiensis*, formed to systematically classify *B. thuringiensis* crystal proteins. The inventors contemplate that the arbitrarily assigned designations of the present invention will be superseded by the official nomenclature assigned to these sequences.

4.7 Transformed Host Cells and Transgenic Plants

Methods and compositions for transforming a bacterium, a yeast cell, a plant cell, or an entire plant with one or more expression vectors comprising a crystal protein-encoding gene segment are further aspects of this disclosure. A transgenic bacterium, yeast cell, plant cell or plant derived from such a transformation process or the progeny and seeds from such a transgenic plant are also further embodiments of the invention.

Means for transforming bacteria and yeast cells are well known in the art. Typically, means of transformation are similar to those well known means used to transform other bacteria or yeast such as *E. coli or Saccharomyces cerevisiae*. Methods for DNA transformation of plant cells include *Agrobacterium*-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

There are many methods for introducing transforming DNA segments into cells, but not all are suitable for delivering DNA to plant cells. Suitable methods are believed to include virtually any method by which DNA can be introduced into a cell, such as by *Agrobacterium* infection, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introduction of DNA into cells is well-known to those of skill in the art. Four general methods for delivering a gene into cells have been described: (1) chemical methods (Graham and van der Eb, 1973; Zatloukal et al., 1992); (2) physical methods such as microinjection (Capecchi, 1980), electroporation (Wong and Neumann, 1982; Fromm et al., 1985; U.S. Pat. No. 5,384,253) and the gene gun (Johnston and Tang, 1994; Fynan et al., 1993); (3) viral vectors (Clapp, 1993; Lu et al., 1993; Eglitis and Anderson, 1988a; 1988b); and (4) receptor-mediated mechanisms (Curiel et al., 1991; 1992; Wagner et al., 1992).

4.7.1 Electroporation

The application of brief, high-voltage electric pulses to a variety of animal and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by means of electroporation, is well-known to those of skill in the art. In this method, certain cell wall-degrading enzymes, such as pectin-degrading enzymes, are employed to render the target recipient cells more susceptible to transformation by electroporation than untreated cells. Alternatively, recipient cells are made more susceptible to transformation, by mechanical wounding. To effect transformation by electroporation one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner. Such cells would then be recipient to DNA transfer by electroporation, which may be carried out at this stage, and transformed cells then identified by a suitable selection or screening protocol dependent on the nature of the newly incorporated DNA.

4.7.2 Microprojectile Bombardment

A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like.

An advantage of microprojectile bombardment, in addition to it being an effective means of reproducibly stably transforming monocots, is that neither the isolation of protoplasts (Cristou et al., 1988) nor the susceptibility to *Agrobacterium* infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with corn cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

4.7.3 *Agrobacterium*-mediated Transfer

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described (Fraley et al., 1985; Rogers et al., 1987). Further, the integration of the Ti-DNA is a relatively precise process resulting in few rearrangements. The region of DNA to be transferred is defined by the border sequences, and intervening DNA is usually inserted into the plant genome as described (Spielmann et al., 1986; Jorgensen et al., 1987).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate construction of vectors capable of expressing various polypeptide coding genes. The vectors described (Rogers et al., 1987), have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

*Agrobacterium*-mediated transformation of leaf disks and other tissues such as cotyledons and hypocotyls appears to be limited to plants that *Agrobacterium* naturally infects. *Agrobacterium*-mediated transformation is most efficient in dicotyledonous plants. Few monocots appear to be natural hosts for Agrobacterium, although transgenic plants have been produced in asparagus using Agrobacterium vectors as described (Bytebier et al., 1987). Therefore, commercially important cereal grains such as rice, corn, and wheat must usually be transformed using alternative methods. However, as mentioned above, the transformation of asparagus using *Agrobacterium* can also be achieved (see, for example, Bytebier et al., 1987).

A transgenic plant formed using Agrobacterium transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous gene segregates independently during mitosis and meiosis.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for enhanced carboxylase activity relative to a control (native, non-transgenic) or an independent segregant transgenic plant.

It is to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated.

4.7.4 Other Transformation Methods

Transformation of plant protoplasts can be achieved using methods based on calcium phosphate precipitation, polyethylene glycol treatment, electroporation, and combinations of these treatments (see, e.g., Potrykus et al., 1985; Lorz et al., 1985; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts are described (Fujimura et al., 1985; Toriyama et al., 1986; Yamada et al., 1986; Abdullah et al., 1986).

To transform plant strains that cannot be successfully regenerated from protoplasts, other ways to introduce DNA into intact cells or tissues can be utilized. For example, regeneration of cereals from immature embryos or explants can be effected as described (Vasil, 1988). In addition, "particle gun" or high-velocity microprojectile technology can be utilized. (Vasil, 1992)

Using that latter technology, DNA is carried through the cell wall and into the cytoplasm on the surface of small metal particles as described (Klein et al., 1987; Klein et al., 1988; McCabe et al., 1988). The metal particles penetrate through several layers of cells and thus allow the transformation of cells within tissue explants.

4.8 Methods for Producing Insect-resistant Transgenic Plants

By transforming a suitable host cell, such as a plant cell, with a recombinant cryET33 and/or cryET34 gene-containing segment, the expression of the encoded crystal protein (i.e., a bacterial crystal protein or polypeptide having insecticidal activity against coleopterans) can result in the formation of insect-resistant plants.

By way of example, one may utilize an expression vector containing a coding region for a *B. thuringiensis* crystal protein and an appropriate selectable marker to transform a suspension of embryonic plant cells, such as wheat or corn cells using a method such as particle bombardment (Maddock et al., 1991; Vasil et al., 1992) to deliver the DNA coated on microprojectiles into the recipient cells. Transgenic plants are then regenerated from transformed embryonic calli that express the insecticidal proteins.

The formation of transgenic plants may also be accomplished using other methods of cell transformation which are known in the art such as *Agrobacterium*-mediated DNA transfer (Fraley et al., 1983). Alternatively, DNA can be introduced into plants by direct DNA transfer into pollen (Zhou et al., 1983; Hess, 1987; Luo et al., 1988), by injection of the DNA into reproductive organs of a plant (Pena et al., 1987), or by direct injection of DNA into the cells of immature embryos followed by the rehydration of desiccated embryos (Neuhaus et al., 1987; Benbrook et al., 1986).

The regeneration, development, and cultivation of plants from single plant protoplast transformants or from various transformed explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by *Agrobacterium* from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983).

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, as discussed before. Otherwise, pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A transgenic plant of this invention thus has an increased amount of a coding region (e.g., a cry gene) that encodes the Cry polypeptide of interest. A preferred transgenic plant is an independent segregant and can transmit that gene and its activity to its progeny. A more preferred transgenic plant is homozygous for that gene, and transmits that gene to all of its offspring on sexual mating. Seed from a transgenic plant may be grown in the field or greenhouse, and resulting sexually mature transgenic plants are self-pollinated to generate true breeding plants. The progeny from these plants become true breeding lines that are evaluated for, by way of example, increased insecticidal capacity against coleopteran insects, preferably in the field, under a range of environmental conditions. The inventors contemplate that the present invention will find particular utility in the creation of transgenic plants of commercial interest including various turf grasses, wheat, corn, rice, barley, oats, a variety of ornamental plants and vegetables, as well as a number of nut- and fruit-bearing trees and plants.

5. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Isolation of B. thuringiensis EG10327

Crop dust samples were obtained from various sources throughout the U.S. and abroad, typically grain storage facilities. The crop dust samples were treated and spread on agar plates to isolate individual *Bacillus*-type colonies as described in U.S. Pat. No. 5,264,364.

The cloned cryIIIA gene, formerly known as the cryC gene of *B. thuringiensis* strain EG2158, described in Donovan et al., (1988), and the cloned cryIIIB2 gene, formerly known as the cryIIIC gene of *B. thuringiensis* strain EG4961, described in Donovan et al., 1992, were used as probes in colony hybridization procedures. The cryIIIA gene probe consisted of a radioactively labeled 2.0 kb HindIII-XbaI DNA restriction fragment as described in Donovan et al., 1988. The cryIIIB2 gene probe consisted of a radioactively labeled 2.4 kb SspI DNA restriction fragment as described in Donovan et al., 1992. The colony hybridization procedures were performed as described in U.S. Pat. No. 5,264,364.

Approximately 43,000 *Bacillus*-type colonies from fifty-four crop dust samples from various locations were probed with the radioactively-labeled cryIIIA and cryIIIB2 probes. One crop dust sample from Greece contained approximately 100 naturally-occurring *Bacillus*-type colonies that hybridized with the cryIIIA and cryIIIB2 probes. Analysis of several of these naturally-occurring, wild-type colonies indicated that they were identical *B. thuringiensis* colonies, and one colony, designated EG 10327, was selected for further study. *B. thuringiensis* strain EG10327 was deposited on Dec. 14, 1994 under the terms of the Budapest Treaty with the NRRL under Accession No. NRRL B-21365.

Subsequently approximately 84,000 *Bacillus*-type colonies from 105 crop dust samples from various locations were also screened with the radioactively-labeled cryIIIA and cryIIIB2 probes, but without success in identifying any other strains containing novel cryIII-type genes.

*B. thuringiensis* strain EG10327 was found to be insecticidally-active against the larvae of coleopteran insects, notably, the red flour beetle, the boll weevil, and the Japanese beetle. Strain EG10327 did not have measurable insecticidal activity with respect to the southern corn rootworm or the Colorado potato beetle under the assay conditions used. A gene, designated "cryIIIA-truncated", was isolated from strain EG 10327, and its nucleotide base sequence determined. The cryIIIA-truncated gene was found to be identical with the first two-thirds of the cryIIIA gene (described as the cryC gene in Donovan et al., 1988) but did not contain the final one-third of the cryIIIA gene. The truncated cryIIIA gene of strain EG10327 produced very little, if any, insecticidal protein and was not further characterized.

5.2 Example 2

Evaluation of the Flagellar Serotype of EG10327

To characterize strain EG 10327 several studies were conducted. One study was performed to characterize its flagellar serotype. These data are provided below.

The flagellar serotype of strain EG10327 was determined in the laboratory of Dr. M.-M. Lecadet at the Pasteur Institute, Paris, France. The serotype of EG10327 was determined according to methods described by H. de Barjac (1981), and was found to be *Bacillus thuringiensis kurstaki* (H3a, 3b, 3c). Previously described *B. thuringiensis* strains containing cryIII-related genes were found to be serotype *morrisoni* (strain EG2158 containing cryIIIA); serotype *tolworthi* (strain EG2838 containing cryIIIB); and serotype *kumamotoensis* (strain EG4961 containing cryIIIB2) (Rupar et al., 1991). EG10327 represents the first *B. thuringiensis kurstaki* strain that has been shown to be toxic to coleopterans.

5.3 Example 3

Evaluation of the Crystal Proteins of EG10327

Strain EG10327 was further evaluated by characterizing the crystal proteins it produces. These studies were performed by growing EG10327 in DSG sporulation medium [0.8% (wt./vol.) Difco nutrient broth, 0.5% (wt./vol.) glucose, 10 mM $K_2HPO_4$, 10 mM $KH_2PO_4$, 1 mM $Ca(NO_3)_2$, 0.5 mM $MgSO_4$, 10 µM $MnCl_2$, 10 µM $FeSO_4$]. The sporulated culture containing both spores and crystal proteins was then harvested by centrifugation and suspended in deionized water. Crystal proteins were solubilized from the suspension of EG10327 spores and crystals by incubating the suspension in solubilization buffer [0.14 M Tris pH 8.0, 2% (wt./vol.) sodium dodecyl sulfate (SDS), 5% (vol./vol.) 2-mercaptoethanol, 10% (vol./vol.) glycerol and 0.1% (wt./vol.) bromophenol blue] at 100° C. for 5 min.

The solubilized crystal proteins were size fractionated by electrophoresis through an acrylamide gel (SDS-PAGE analysis). After size fractionation, the proteins were visualized by staining with Coomassie dye. SDS-PAGE analysis showed that a major crystal protein of approximately 29 kDa, hereinafter referred to as the CryET33 protein, and a major crystal protein of approximately 14 kDa, hereinafter referred to as the CryET34 protein, were solubilized from the sporulated EG 10327 culture.

The 29-kDa CryET33 protein and the 14-kDa CryET34 protein of EG10327 were further characterized by determination of their $NH_2$-terminal amino acid sequences as follows. The sporulated EG10327 culture was incubated with solubilization buffer and solubilized crystal proteins were size fractionated through an acrylamide gel by SDS-PAGE analysis. The proteins were transferred from the gel to a nitrocellulose filter by standard electroblotting techniques. The CryET33 protein and the CryET34 protein that had been electroblotted to the filter were visualized by staining the filter with Coomassie dye. Portions of the filter containing the CryET33 protein and the CryET34 protein were excised with a razor blade. In this manner the CryET33 protein and the CryET34 protein were obtained in pure forms as proteins blotted onto separate pieces of nitrocellulose filter.

The purified CryET33 and CryET34 proteins contained on pieces of nitrocellulose filter were subjected to a standard automated Edman degradation procedure in order to determine the $NH_2$-terminal amino acid sequence of each protein.

The $NH_2$-terminal sequence of the CryET33 protein of EG10327 was found to be:

```
                                                              (SEQ ID NO:5)
 1  2  3  4  5  6  7  8  9 10 11 12 13 14 15 16 17 18 19 20
GlyIleIleAsnIleGlnAspGluIleAsnAsnTyrMetLysGluValTyrGlyAlaThr
```

The NH₂-terminal sequence of the CryET34 protein of EG10327 was found to be:

```
                                                              (SEQ ID NO:6)
 1  2  3  4  5  6  7  8  9 10 11 12 13 14 15 16 17 18 19 20
ThrValTyrAsnValThrPheThrIleLysPheTyrAsnGluGlyGluTrpGlyGlyPro
            (Ala)           (Asn)
```

The amino acid residues listed in parenthesis below the sequence of the CryET34 protein represent potential alternative amino acids that may be present in the CryET34 protein at the position indicated. Alternative amino acids are possible due to the inherent uncertainty that exists in the use of the automated Edman degradation procedure for determining protein amino acid sequences.

Computer algorithms (Korn and Queen, 1984) were used to compare the N-terminal sequences of the CryET33 and CryET34 proteins with amino acid sequences of all *B. thuringiensis* crystal proteins of which the inventors are aware including the sequences of all *B. thuringiensis* crystal proteins which have been published in scientific literature, international patent applications, or issued patents. A list of the crystal proteins whose sequences have been published along with the source of publication is shown in Table 5.

TABLE 5

*B. THURINGIENSIS* CRYSTAL PROTEINS DESCRIBED IN THE LITERATURE

| Crystal Protein | Source or Reference |
|---|---|
| Cry1A(a) | J. Biol. Chem., 260: 6264-6272 |
| Cry1A(b) | DNA, 5: 305-314 |
| Cry1A(c) | Gene, 36: 289-300 |
| Cry1B | Nucl. Acids Res., 16: 4168-4169 |
| Cry1C | Nucl. Acids Res., 16: 6240 |
| Cry1Cb | Appl. Environ. Micro., 59: 1131-1137 |
| Cry1C(b) | Nucl. Acids Res., 18: 7443 |
| Cry1D | Nucl. Acids Res., 18: 5545 |
| Cry1E | EPO 358 557 A2 |
| Cry1F | J. Bacteriol., 173: 3966-3976 |
| Cry1G | FEBS, 293: 25-28 |
| CryV | WO 90/13651 |
| Cry2A | J. Biol. Chem., 263: 561-567 |
| Cry2B | J. Bacteriol., 171: 965-974 |
| Cry2C | FEMS Microbiol. Lett., 81: 31-36 |
| Cry3A | Proc. Natl. Acad Sci. USA, 84: 7036-7040 |
| Cry3B | Nucl. Acids Res., 18: 1305 |
| Cry3B2 | Appl. Environ. Microbiol., 58: 3921-3927 |
| Cry3B3 | U.S. Pat. No. 5,378,625 |
| Cry3C | Appl. Environ. Microbiol., 58: 2536-2542 |
| Cry3D | Gene, 110: 131-132 |
| Cry4A | Nucl. Acids Res., 15: 7195 |
| Cry4B | EPO 308,199 |
| Cry4C | J. Bacteriol., 166: 801-811 |
| Cry4D | J. Bacteriol., 170: 4732, 1988 |
| Cry5 | Molec. Micro., 6: 1211-1217 |
| Cry33AkD | WO 94/13785 |
| Cry33BkD | WO 94/13785 |
| Cry34kD | J. Bacteriol., 174: 549-557 |
| Cry40kD | J. Bacteriol., 174: 549-557 |
| Cry201T635 | WO 95/02693 |
| Cry517 | J. Gen. Micro., 138: 55-62 |
| Crya7A021 | EPO 256,553 B1 |
| CryAB78ORF1 | WO 94/21795 |
| CryAB780RF2 | WO 94/21795 |

TABLE 5-continued

*B. THURINGIENSIS* CRYSTAL PROTEINS DESCRIBED IN THE LITERATURE

| Crystal Protein | Source or Reference |
|---|---|
| CryAB78100kD | WO 94/21795 |
| Crybtpgs1208 | EPO 382 990 |
| Crybtpgs 1245 | EPO 382 990 |
| Crybts02618A | WO 94/05771 |
| CryBuibui | WO 93/03154 |
| CryET4 | U.S. Pat. No. 5,322,687 |
| CryET5 | U.S. Pat. No. 5,322,687 |
| CryGei87 | EPO 238,441 |
| CryHD511 | U.S. Pat. No. 5,286,486 |
| CryHD867 | U.S. Pat. No. 6,286,486 |
| CryIPL | U.S. Pat. No. 5,231,008 |
| CryMITS | JP 6000084 |
| CryPS17A | WO 92/19739 |
| CryPS17B | U.S. Pat. No. 5,350,576 and U.S. Pat. No. 5,424,410 |
| CryP16 | WO 95/00639 |
| CryP18 | WO 95/00639 |
| CryP66 | WO 95/00639 |
| CryPS33F2 | WO 92/19739 and U.S. Pat. No. 5,424,410 |
| CryPS40D1 | U.S. Pat. No. 5,273,746 |
| CryPS43F | WO 93/04587 |
| CryPS 50Ca | WO 93/04587 and EPO 498,537 A2 |
| CryPS 50Cb | WO 93/15206 |
| Cryps52A1 | U.S. Pat. No. 4,849,217 |
| CryPS63B | WO 92/19739 |
| CryPS69D1 | U.S. Pat. No. 5,424,410 |
| Cryps71M3 | WO 95/02694 |
| CryPS80JJ1 | WO 94/16079 |
| CryPS81IA | U.S. Pat. No. 5,273,746 |
| CryPS81IA2 | EPO 405 810 |
| Cryps81A2 | EPO 401 979 |
| CryPS81IB | WO 93/14641 |
| CryPS81IB2 | U.S. Pat. No. 5,273,746 |
| Cryps81f | U.S. Pat. No. 5,045,469 |
| Cryps81gg | U.S. Pat. No. 5,273,746 |
| Cryps81rr1 | EPO 401 979 |
| Cryps86A1 | U.S. Pat. No. 5,468,636 |
| CryX | FEBS Lett., 336: 79-82 |
| CryXenA24 | WO 95/00647 |
| CrycytA | Nucl. Acids Res., 13: 8207-8217 |

The N-terminal sequence of the CryET34 of EG10327 protein was not found to be homologous to any of the known *B. thuringiensis* crystal proteins identified in Table 5.

5.4 Example 4

Characterization of the CryET33 Crystal Protein of EG2159

It had been previously determined that the 68-kDa CryIIIA protein of EG2159 (referred to as the CryC protein in Donovan et al., 1988) was toxic to Colorado potato beetle, but no protein had been identified in the strain which had lepidopteran or dipteran activity.

Strain EG2159 was derived from *B. thuringiensis* strain EG2158 by curing of a 150-MDa plasmid from EG2158 (described in Donovan et al., 1988). EG2159 is identical to EG2158 except that EG2159 is missing a 150-MDa plasmid present in EG2158. One of the two crystal proteins produced by EG2159, the 68-kDa CryIIIA protein, was isolated, and the gene encoding it was cloned and sequenced. These results were described previously by the inventors (Donovan et al., 1988). A minor protein species, a 29-kDa protein of EG2159, was not further characterized.

This example describes the characterization of this 29-kDa CryET33 crystal protein from *B. thuringiensis* EG2159.

5.4.1 Isolation of Crystal Proteins from EG2159

The crystal proteins of EG2159 were solubilized by suspending a sporulated culture of EG2159 containing spores plus crystal proteins in protein solubilization buffer at 80° C. for 3 min. The solubilized crystal proteins were size fractionated by SDS-PAGE and proteins in the SDS-PAGE gel were visualized by staining with Coomassie dye. Gel slices containing the 29-kDa protein were cut out of the SDS-PAGE gel with a razor blade and the protein was separated from the gel slices by standard electroelution procedures. These studies resulted in a purified preparation of the CryET33 protein from *B. thuringiensis* strain EG2159.

5.4.2 $NH_2$-Terminal Sequencing of the 29kDa Protein

The $NH_2$-terminal amino acid sequence of the purified CryET33 protein was determined by automated Edman degradation. The amino acid sequence of the $NH_2$-terminal portion of the 29-kDa protein was determined to be:

```
                              (SEQ ID NO:7) (SEQ ID NO:8)
1  2  3  4  5  6  7  8  9  10 11 12 13 14 15 16 17 18 19 20
MetGlyIleIleAsnIleGlnAspGluIleAsn---TyrMetLysGluValTyrGlyAla
```

Dashes (---) at position 12 indicate that this amino acid residue could not be determined for the CryET33 protein of EG2159.

5.4.3 Results

Comparison of the sequence of the CryET33 protein of EG 10327 (SEQ ID NO:5) and the $NH_2$-terminal sequence of the previously-uncharacterized 29-kDa protein (Donovan et al., 1988) observed in EG2159 (SEQ ID NO:7, SEQ ID NO:8) suggested that the $NH_2$-terminal end of the 29-kDa protein of EG2159 was identical to the CryET33 protein of EG10327, with the exception of an initial methionine (Met) residue present in the CryET33 protein of EG2159.

5.5 Example 5

Isolation of a DNA Fragment Comprising CryET33 and CryET34 Genes from EG2158

As described above, strain EG2159 was derived from strain EG2158. Therefore, EG2158 contains the identical gene for the CryET33 protein, hereinafter referred to as the cryET33 gene, as strain EG2159. To clone the cryET33 gene reverse genetics was used. A 33-mer oligonucleotide probe (designated WD68) encoding amino acids 1 through 11 of the $NH_2$-terminus of the CryET33 protein was synthesized. The sequence of WD68 is:

```
                                      (SEQ ID NO:9)
5'-ATGGGAATTATTAATATTCAAGATGAAATTAAT-3'
```

WD68 was used as a probe in Southern hybridization studies as described below in attempts to identify a DNA fragment from EG2158 that contained the cryET33 gene for the 29-kDa CryET33 protein. Total DNA was extracted from EG2158 by a standard lysozyme/phenol method. The extracted DNA was digested with DNA restriction enzymes HindIII and EcoRI, and the digested DNA was size fractionated by electrophoresis through an agarose gel. The DNA fragments were blotted from the gel to a nitrocellulose filter using previously described methods (Southern, 1975), and the filter was incubated with oligonucleotide WD68 that had been radioactively labeled with T4 kinase and [$\gamma$-$^{32}$P]ATP. No unique DNA restriction fragment from EG2158 was found to which the WD68 probe specifically hybridized.

A different approach was then used to identify a DNA restriction fragment that contained the cryET33 gene. A 56-mer oligonucleotide probe (designated WD73) encoding amino acids 1 through 19 of the $NH_2$-terminus of the CryET33 protein was synthesized. The sequence of WD73 is:

(SEQ ID NO:10)
5'-ATGGGAATTATTAATATTCAAGATGAAATTAATNNNTATATGAAAGAAGTATATGG-3' where the three N's corresponding to amino acid 12 of WD73 represent three inosine nucleotides. Inosine residues were used at this position to encode the corresponding unknown amino acid at position 12 in the $NH_2$-terminal sequence of the CryET33 protein. Inosine is considered to be a neutral nucleotide, and neither promotes nor hinders binding of DNA strands. WD73 was radioactively labeled with T4 kinase and [$\gamma$-$^{32}$P]ATP and used to probe a nitrocellulose filter containing size-fractionated HindIII and EcoRI restriction fragments of EG2158 total DNA. WD73 specifically hybridized to a HindIII fragment of approximately 7.9 kb, and to an EcoRI fragment of approximately 5.2-kb of EG2158 DNA.

5.6 Example 6

Cloning of the CryET33 and CryET34 Genes form EG2158

To isolate the 5.2-kb EcoRI fragment described in the previous Example, a plasmid library of strain EG2158 was constructed by ligating size-selected DNA EcoRI restriction fragments from strain EG2158 into the *E. coli* vector pBR322. This procedure involved first obtaining total DNA from strain EG2158 by cell lysis followed by phenol extraction of DNA, then digesting the total DNA with EcoRI restriction enzyme, electrophoresing the digested DNA through an agarose gel, excising a gel slice containing EcoRI DNA fragments ranging in size from approximately 4.0 to 6.0 kb, and electroeluting the size selected EcoRI restriction fragments from the agarose gel slice. These fragments were mixed with the *E. coli* plasmid vector pBR322, which had also been digested with EcoRI. The pBR322 vector carries the gene for $Amp^R$ and the vector replicates in *E. coli*. T4 DNA ligase and ATP were added to the mixture of size-selected restriction fragments of DNA from strain EG2158 and of digested pBR322 vector to allow the pBR322 vector to ligate with strain EG2158 restriction fragments.

The plasmid library was then transformed into *E. coli* cells, a host organism lacking the cryET33 and cryET34 genes of interest as follows. After ligation, the DNA mixture was incubated with an $Amp^S$ *E. coli* host strain, HB101, that had been made competent using standard $CaCl_2$ procedures. *E. coli* HB101, was used as the host strain because these cells are easily transformed with recombinant plasmids and because HB101 does not naturally contain genes for *B. thuringiensis* crystal proteins. Since pBR322 expresses $Amp^R$, all host cells acquiring a recombinant plasmid were $Amp^R$. After transforming host cells with the recombinant plasmids, cells were spread on agar medium that contained Amp. After incubation overnight at a temperature of 37° C., several thousand *E. coli* colonies grew on the Amp-containing agar, and these colonies were then blotted onto nitrocellulose filters for subsequent probing.

The radioactively-labeled oligonucleotide WD73 was then used as a DNA probe under conditions that permitted the probe to bind specifically those transformed host colonies that contained the 5.2-kb EcoRI fragment of DNA from strain EG2158. Several *E. coli* colonies specifically hybridized to the WD73 probe. One WD73-hybridizing colony, designated *E. coli* EG11460, was studied further. *E. coli* EG11460 contained a recombinant plasmid, designated pEG246, which consisted of pBR322 plus the inserted EcoRI restriction fragment of DNA from strain EG2158 of approximately 5.2 kb. A restriction map of pEG246 is shown in FIG. 2. The *E. coli* strain EG 11460 containing pEG246 has been deposited with the Agricultural Research Culture Collection, Northern Regional Research Laboratory (NRRL) under the terms of the Budapest Treaty having Accession No. NRRL B-21364.

The nucleotide base sequence of approximately one-third of the cloned 5.2-kb EcoRI fragment of pEG246 was determined using the standard Sanger dideoxy method. Sequencing revealed that the 5.2-kb fragment contained two adjacent open reading frames encoding proteins and, in particular, two novel crystal toxin genes. The upstream open reading frame, designated cryET33, encoded a protein whose $NH_2$-terminal sequence matched the $NH_2$-terminal sequence of the 29-kDa CryET33 protein of strains EG2159 and EG10327. The downstream gene, designated cryET34, encoded a protein whose amino acid sequence matched the $NH_2$-terminal amino acid sequence determined for the 14 kDa CryET34 protein of EG10327. The DNA sequences of these new genes are significantly different from the sequences of the known crystal toxin genes of *B. thuringiensis* listed in Table 5.

The DNA sequence of the cryET33 gene (SEQ ID NO:1) and the deduced amino acid sequence of the CryET33 protein (SEQ ID NO:3) encoded by the cryET33 gene are shown in FIG. 1A, FIG. 1B, and FIG. 1C. The protein coding portion of the cryET33 gene (SEQ ID NO:1) is defined by the nucleotides starting at position 136 and ending at position 936. The size of the CryET33 protein (SEQ ID NO:3) as deduced from the cryET33 gene (SEQ ID NO:1) is 29,216 Da (267 amino acids). Also shown in FIG. 1A, FIG. 1B, and FIG. 1C are the DNA sequence of the cryET34 gene (SEQ ID NO:2) and the deduced amino acid sequence of the CryET34 protein (SEQ ID NO:4) encoded by the cryET34 gene. The protein coding portion of the cryET34 gene (SEQ ID NO:2) is defined by the nucleotides starting at position 969 and ending at position 1346. The size of the CryET34 protein (SEQ ID NO:4) as deduced from the cryET34 gene (SEQ ID NO:2) is 14,182 Da (126 amino acids).

Computer algorithms (Korn and Queen, 1984; Altschul et al., 1990) were used to compare the DNA sequences of the cryET33 and cryET34 genes and the deduced amino acid sequences of the CryET33 and CryET34 proteins to the sequences of all *B. thuringiensis* cry genes and crystal proteins of which the inventors are aware (described in section 5.3, Example 3, and listed in Table 5) and to the sequences of all genes and proteins contained in the Genome Sequence Data Base (National Center for Genome Resources, Santa Fe, N. Mex). The sequence of the cryET34 gene (SEQ ID NO:2) and the deduced sequence of the CryET34 protein (SEQ ID NO:4) were not found to be related to any known genes or proteins, respectively. The sequence of the cryET33 gene (SEQ ID NO:1) was found to have sequence identity with only one known gene and the sequence identity was very low. The sequence of the cryET33 gene (801 nucleotides) was 38% identical with the sequence of a *B. thuringiensis* subsp. thompsoni gene (1,020 nucleotides) described by Brown and Whiteley (1992). The deduced sequence of the CryET33 protein (SEQ ID NO:3) was found to have sequence identity with only one known protein and the identity was very low. The complete amino acid sequence of the CryET33 protein (267 amino acids) was found to be 27% identical with the complete amino acid sequence of a *B. thuringiensis* subsp. *thompsoni* crystal protein (340 amino acids) described by Brown and Whiteley, 1992 for a caterpillar-toxic protein.

The DNA sequence immediately upstream from the cryET33 gene (FIG. 1A, FIG. 1B, and FIG. 1C, nucleotides 1 to 135) was searched for homologies with all known upstream DNA sequences of crystal protein genes and with the DNA sequences of all known genes in the Genome Sequence Database (Table 5). DNA sequences immediately upstream from coding regions of genes often contain promoters for expression of the corresponding genes. This search resulted in no homologies being found.

5.7 Example 7

Expression of Recombinant CryET33 and CryET34 Genes

Experience has shown that cloned *B. thuringiensis* crystal toxin genes are poorly expressed in *E. coli* but are often highly expressed in recombinant *B. thuringiensis* strains. pEG246, containing the cryET33 and cryET34 genes (FIG. 2), is capable of replicating in *E. coli* but not in *B. thuringiensis*. To obtain a plasmid containing the cryET33 and cryET34 genes and capable of replicating in *B. thuringiensis*, a *Bacillus* spp. plasmid was inserted into pEG246 as described below.

The *Bacillus* spp. plasmid pNN101 (Norton et al., 1985) capable of replicating in *B. thuringiensis* and conferring chloramphenicol resistance ($Cam^R$) and tetracycline resistance ($Tet^R$) was digested with BamHI and the digested plasmid was mixed with plasmid pEG246 that had been digested with BamHI. The two plasmids were ligated together with T4 ligase plus ATP. The ligation mixture was then used to transform competent *E. coli* DH5ac cells. After incubation with the plasmid mixture the cells were plated on agar plates containing Tet. It was expected that cells which had taken up a plasmid consisting of pNN101 ligated with pEG246 would be $Tet^R$. After incubation for approximately 20 hr several $Tet^R$ *E. coli* colonies grew on the agar plates containing Tet.

Plasmid DNA was isolated from one $Tet^R$ colony. The plasmid was digested with BamHI, and electrophoresed through an agarose gel. The plasmid, which was designated pEG1246, consisted of two BamHI DNA fragments of 5.8 kb and 9.6 kb corresponding to plasmids pNN101 and pEG246, respectively. A restriction map of pEG 1246 is shown in FIG. 3.

*B. thuringiensis* strain EG 10368 was then transformed by electroporation with pEG1246 using previously described methods (Macaluso and Mettus, 1991). Untransformed host cells of EG10368 are crystal negative ($Cry^-$) and $Cam^S$. After electroporation, the transformation mixture was spread onto an agar medium containing Cam and were incubated approximately 16 hr at 30° C. pEG1246-transformed cells would $Cam^R$. One $Cam^R$ colony, designated *B. thuringiensis* strain EG11403, contained a plasmid whose restriction pattern was identical to that of pEG1246.

Cells of strain EG11403 were grown in DSG sporulation medium containing Cam at 22° C. to 25° C. until sporulation and cell lysis had occurred (4-5 days). Microscopic examination revealed that the sporulated culture of strain EG11403 contained spores and small free floating spindle-shaped and irregularly shaped crystals. The crystals resembled those observed with a sporulated culture of strain EG10327.

Spores, crystals and cell debris from the sporulated culture of strain EG11403 were harvested by centrifugation. The centrifuge pellet was washed once with deionized water, and the pellet suspended in deionized water.

Crystal proteins in the EG11403 suspension were characterized by solubilization and SDS-PAGE analysis. SDS-PAGE analysis revealed that strain EG11403 produced two major proteins of 29 kDa and 14 kDa. As expected the 29 kDa protein and the 14-kDa protein of strain EG11403 were identical in size to the 29-kDa CryET33 protein and to the 14-kDa CryET34 protein, respectively, produced by strain EG10327. Strain EG11403 was deposited on Dec. 14, 1994, with the Agricultural Research Culture Collection, Northern Regional Research Laboratory (NRRL) under the terms of the Budapest Treaty having Accession No. NRRL B-21367.

The gene encoding the 29 kDa CryET33 protein of EG11403 is the cryET33 gene and the gene encoding the 14 kDa CryET34 protein of EG11403 is the cryET34 gene. *B. thuringiensis* strains EG11403 and EG10327 produced approximately equal amounts of CryET33 protein. In contrast, *B. thuringiensis* strain EG2158 produced approximately $1/10^{th}$ the amount of the CryET33 protein as either strain EG11403 or strain EG10327.

5.8 Example 8

*B. thuringiensis* EG11402 Containing CryIIIB3, CryET33 and CryET34

It was previously shown that the *B. thuringiensis* crystal protein designated as CryIIIB3 was toxic to larvae of the Japanese beetle (U.S. Pat. No. 5,264,364). In the following example, the CryET33 and CryET34 proteins were found to be toxic to boll weevil, and Japanese beetle larvae. The Cry3B3 protein shares no amino acid sequence homology with either the CryET33 protein or the CryET34 protein. In an attempt to produce a strain having enhanced Japanese beetle toxicity the cry3B3 gene, the cryET33 gene, and the cryET34 gene were combined in one strain as follows.

Strain EG]0364 is a wild-type *B. thuringiensis* strain containing the cryIIIB3 gene. EG10364 produces the Japanese beetle larvae-toxic Cry3B3 protein. pEG1246 (FIG. 3) containing the cryET33 and cryET34 genes was used to transform EG10364 by electroporation to give rise to strain EG11402. EG11402 is identical to EG10364 except that EG11402 also contains pEG 1246 (bearing the cloned cryET33 and cryET34 genes), and is consequently $Cam^R$.

Strain EG11402 was grown in DSG sporulation medium plus Cam at room temp. until sporulation and cell lysis occurred (4-5 days). Crystal proteins were solubilized from the sporulated EG11402 culture and the solubilized proteins were size fractionated by SDS-PAGE. This analysis revealed that strain EG11402 produced three crystal proteins: a 70-kDa crystal protein corresponding to the CryIIIB3 protein, a 29-kDa crystal protein corresponding to the CryET33 protein, and a 14-kDa crystal protein corresponding to the CryET34 protein. SDS-PAGE analysis showed that strain EG10364, which had been grown in an identical manner as EG11402 except without chloramphenicol, produced the 70-kDa CryIIIB3 protein in similar amounts as EG11402. Strain EG11402 was deposited on Dec. 14, 1994 under the terms of the Budapest Treaty with the Agricultural Research Culture Collection, Northern Regional Research Laboratory (NRRL) having Accession No. NRRL B-21366.

5.9 Example 9

Toxicity of CryET33 and CryET34 to Japanese Beetle Larvae

The toxicity to Japanese beetle larvae (*Popillia japonica*) was determined for three *B. thuringiensis* strains: (1) strain EG10327 producing the CryET33 and CryET34 crystal proteins; (2) strain EG10364 producing the Cry3B3 crystal protein; and (3) strain EG11402 producing the CryET33, CryET34 and Cry3B3 crystal proteins.

Strains EG10327, EG10364, and EG11402 were grown in DSG sporulation medium at room temperature (20 to 23° C.) until sporulation and cell lysis had occurred (4-5 days). For EG11402, the medium contained 5 µg/ml Cam. The fermentation broth was concentrated by centrifugation and the pellets, containing spores, crystal proteins and cell debris were either freeze dried to yield powders or were resuspended in deionized water to yield aqueous suspensions. The amounts of the Cry3B3 and CryET33 crystal proteins in the freeze-dried powders and in the suspensions were quantified using SDS-PAGE techniques and densitometer tracing of Coomassie stained SDS-PAGE gels with purified and quantified Cry3A protein as a standard. The amount of the CryET34 protein was estimated by visual inspection of Coomassie stained SDS-PAGE gels. This inspection indicated that the amount of the CryET34 protein was roughly equivalent to the amount of the CryET34 protein in strains EG10327 and EG11402.

The bioassay procedure for Japanese beetle larvae was carried out as follows. freeze-dried powders of each strain to be tested were suspended in a diluent (an aqueous solution containing 0.005% Triton X-100®) and were incorporated into 100 ml of hot (50-60° C.) liquid artificial diet, based on the insect diet previously described (Ladd, 1986). The mixtures were allowed to solidify in Petri dishes, and 19-mm diameter plugs of the solidified diet were then placed into ⅝ ounce plastic cups. One Japanese beetle larvae was introduced into each cup, the cups were covered with a lid and held at 25° C. for fourteen days before larvae mortality was scored. Two replications of sixteen larvae each were carried out in this study.

The results of this toxicity test are shown below in Table 6, where insecticidal activity is reported as percentage of dead larvae, with the percent mortality being corrected for control death, the control being diluent only incorporated into the diet plug.

TABLE 6

ACTIVITY OF CRYET33, CRYET34 AND CRY3B3 TO JAPANESE BEETLE LARVAE

| Strain | Protein(s) Present | Protein Dose | Insect Mortality |
| --- | --- | --- | --- |
| EG10327 | CryET33 | ~4,000 ppm | 95% |
|  | CryET34 | ND[a] |  |
| EG10364 | Cry3B3 | 500 ppm | 38% |
| EG11402 | Cry3B3 | 560 ppm | 58% |
|  | CryET33 | ~1,000 ppm |  |
|  | CryET34 | ND |  |

[a]ND, not determined.

The results shown in Table 6 demonstrate that the CryET33 and CryET34 proteins have significant toxicity to Japanese beetle larvae. EG10327, which produces the CryET33 and CryET34 proteins, is toxic to Japanese beetle larvae. EG10364 which produces the Cry3B3 protein is also toxic to Japanese beetle larvae. When the cryET33 and cryET34 genes are added to EG10364, resulting in EG11402 which produces the CryET33 and CryET34 proteins in addition to the Cry3B3 protein, an enhanced toxicity to Japanese beetle larvae was seen.

5.10 Example 10

Toxicity of CryET33 and CryET34 to Red Flour Beetle Larvae

The toxicity to red flour beetle larvae (Tribolium castaneum) was determined for four B. thuringiensis strains: (1) EG10327 producing the CryET33 and CryET34 crystal proteins; (2) EG10364 producing the Cry3B3 crystal protein; (3) EG11403 producing the CryET33 and CryET34 crystal proteins; and (4) EG11402 producing the Cry3B3, CryET33 and CryET34 crystal proteins. The four strains were grown in DSG medium until sporulation and cell lysis had occurred, and aqueous suspensions or freeze dried powders were prepared as described in Example 9. The toxicity of each strain against red flour beetle larvae was determined by applying a known amount of each strain preparation to an artificial diet and feeding the diet to red flour beetle larvae.

The results of this toxicity test are shown in Table 7, where insecticidal activity is reported as percentage insect mortality, with the mortality being corrected for control death, the control being diluent only incorporated into the diet.

TABLE 7

TOXICITY OF CRYET33, CRYET34 AND CRY3B3 PROTEINS TO RED FLOUR BEETLE LARVAE

| Strain | Protein | Protein Dose | Insect Mortality |
| --- | --- | --- | --- |
| EG10327 | CryET33 | ~2,000 ppm | 100% |
|  | CryET34 | ND[a] |  |
| EG10364 | Cry3B3 | 448 ppm | 74% |
| EG11402 | Cry3B3 | 448 ppm | 97% |
|  | CryET33 | ~2,000 ppm |  |
|  | CryET34 | ND |  |
| EG11403 | CryET33 | ~2,000 ppm | 39% |
|  | CryET34 | ND |  |

[a]ND, not determined.

The results shown in Table 7 demonstrate that the CryET33 and CryET34 proteins have a significant level of toxicity to red flour beetle larvae. The naturally occurring strain EG10327 which produces the CryET33 and CryET34 proteins is highly toxic to red flour beetle larvae. EG10364 which produces the Cry3B3 protein is toxic to red flour beetle larvae. EG11403 which produces the CryET33 and the CryET34 proteins is toxic to red flour beetle larvae. When the cryET33 and cryET34 genes are added to EG10364, giving rise to EG11402, an enhanced toxicity to red flour beetle larvae is seen in the resultant strain which produces CryET33, CryET34, and Cry3B3 proteins.

5.11 Example 11

Toxicity of CryET33 and CryET34 on Boil Weevil Larvae

EG 11403 producing the CryET33 and Cry ET34 proteins was grown as described. The protein crystal was washed, solubilized in carbonate buffer, dialyzed and filtered through a 0.2 U acrodisc. The toxicity of the solubilized proteins were then determined by adding a known amount of the proteins to artificial diet and feeding the diet to boll weevil larvae. The results of this toxicity test are shown below, where insecticidal activity is reported as either (1) percent mortality, with the mortality being corrected for control death using a buffer control; or (2) percent mortality+the percent of larvae not developing beyond first instar, with the mortality again being corrected for control death using a buffer control.

The results in Table 8 and Table 9 demonstrate that Cry ET33 and CryET34 proteins have a significant level of toxicity to boll weevil larvae.

TABLE 8

(1) BOLL WEEVIL PERCENT MORTALITY

| μg/ml | % Mortality |
|---|---|
| 40 | 50 |
| 20 | 46.67 |
| 10 | 11.76 |
| 5 | 6.67 |
| 2.5 | 0 |
| 1.25 | 6.67 |
| 0.31 | 0 |
| 0.08 | 10 |

TABLE 9

(2) PERCENT MORTALITY + 1ST INSTARS

| μg/ml | % mortality + 1$^{st}$ instar |
|---|---|
| 40 | 100 |
| 20 | 93.33 |
| 10 | 64.71 |
| 5 | 40 |
| 2.5 | 11.11 |
| 1.25 | 6.67 |
| 0.31 | 5.88 |
| 0.08 | 10 |

6. REFERENCES

The following references, to the extent that they provide exemplary procedural or other detailed supplementary to those set forth herein, are specifically incorporated herein by reference:

U.S. Pat. No. 4,196,265, issued Apr. 1, 1980.
U.S. Pat. No. 4,554,101, issued Nov. 19, 1985.
U.S. Pat. No. 4,683,195, issued Jul. 28, 1987.
U.S. Pat. No. 4,683,202, issued Jul. 28, 1987.
U.S. Pat. No. 4,757,011, issued Jul. 12, 1988.
U.S. Pat. No. 4,766,203, issued Aug. 23, 1988.
U.S. Pat. No. 4,769,061, issued Sep. 6, 1988.
U.S. Pat. No. 4,771,131, issued Sep. 13, 1988.
U.S. Pat. No. 4,797,279, issued Jan. 10, 1989.
U.S. Pat. No. 4,910,016, issued Mar. 20, 1990.
U.S. Pat. No. 4,940,835, issued Feb. 23, 1990.
U.S. Pat. No. 4,965,188, issued Oct. 23, 1990.
U.S. Pat. No. 4,966,765, issued Oct. 30, 1990.
U.S. Pat. No. 4,971,908, issued Nov. 20, 1990.
U.S. Pat. No. 4,996,155, issued Feb. 26, 1991.
U.S. Pat. No. 4,999,192, issued Mar. 12, 1991.
U.S. Pat. No. 5,006,336, issued Apr. 9, 1991.
U.S. Pat. No. 5,024,837 issued Jun. 18, 1991.
U.S. Pat. No. 5,055,293, issued Oct. 8, 1991.
U.S. Pat. No. 5,055,294, issued Oct. 8, 1991.
U.S. Pat. No. 5,128,130, issued Oct. 15, 1991.
U.S. Pat. No. 5,176,995, issued Oct. 15, 1991.
U.S. Pat. No. 5,187,091, issued Oct. 15, 1991.
U.S. Pat. No. 5,264,364, issued Nov. 23, 1993.
U.S. Pat. No. 5,286,486, issued Feb. 15, 1994.
U.S. Pat. No. 5,384,253, issued Jan. 24, 1995.
U.S. Pat. No. 5,441,884, issued Aug. 15, 1995.
Eur. Patent No. 0308199, published Mar. 22, 1989.
Eur. Patent No. 0318143, published May 31, 1989.
Eur. Patent No. 0324254, published Jul. 19, 1989.
Eur. Patent No. 0382990, published Aug. 22, 1990.
Intl. Pat. Appl. Publ. No. WO 90/13651, published Nov. 15, 1990.
Intl. Pat. Appl. Publ. No. WO 91/07481, published May 30, 1991.
Intl. Pat. Appl. Publ. No. WO 91/10725, published Jul. 25, 1991.
Intl. Pat. Appl. Publ. No. WO 91/16433, published Oct. 31, 1991.
Intl. Pat. Appl. Publ. No. WO 93/03154, published Feb. 18, 1993.
Intl. Pat. Appl. Publ. No. WO 94/13785, published Jun. 23, 1994.
Intl. Pat. Appl. Publ. No. WO 94/16079, published Jul. 21, 1994.
Intl. Pat. Appl. Publ. No. WO 95/02693, published Jan. 26, 1995.
Intl. Pat. Appl. Publ. No. WO 95/06730, published Mar. 9, 1995.
Intl. Pat. Appl. Publ. No. WO 95/30752, published Nov. 16, 1995.
Intl. Pat. Appl. Publ. No. WO 95/30753, published Nov. 16, 1995.
Abdullah et al., *Biotechnology,* 4:1087, 1986.
Adelman et al., *DNA,* 2/3:183-193, 1983.
Allen and Choun, "Large unilamellar liposomes with low uptake into the reticuloendothelial system," *FEBS Lett.,* 223:42-46, 1987.
Altschul et al., "Basic local alignment search tool," *J. Mol. Biol.,* 215:403-410, 1990.
Arvidson et al., *Mol. Biol.,* 3:1533-1534, 1989.
Baum et al., *Appl. Environ. Microbiol.,* 56:3420-3428, 1990.
Benbrook et al., *In: Proceedings Bio Expo* 1986, Butterworth, Stoneham, Mass., pp. 27-54, 1986.
Berhnard, *FEMS Microbiol. Lett.,* 33:261-265, 1986.
Bolivar et al., *Gene,* 2:95, 1977.
Brown and Whiteley, *J. Bacteriol.,* 174:549-557, 1992.
Bytebier et al., *Proc. Natl. Acad. Sci. USA,* 84:5345, 1987.
Callis et al., *Genes and Development,* 1: 1183, 1987.
Campbell, *In: Monoclonal Antibody Technology, Laboratory Techniques in Biochemistry and Molecular Biology*, Vol. 13, Burden and Von Knippenberg, Eds. pp. 75-83, Elsevier, Amsterdam, 1984.
Capecchi, "High efficiency transformation by direct microinjection of DNA into cultured mammalian cells," *Cell,* 22(2):479-488, 1980.
Cashmore et al., *Gen. Eng. of Plants*, Plenum Press, New York, 29-38, 1983.
Chambers et al., *J. Bacteriol.,* 173:3966-3976, 1991.
Chang et al., *Nature,* 375:615, 1978.
Chau et al., *Science,* 244:174-181, 1989.
Clapp, "Somatic gene therapy into hematopoietic cells. Current status and future implications," *Clin. Perinatol.,* 20(1): 155-168, 1993.
Couvreur et al., "Nanocapsules, a new lysosomotropic carrier," *FEBS Lett.,* 84:323-326, 1977.
Couvreur, "Polyalkyleyanoacrylates as colloidal drug carriers," *Crit. Rev. Ther. Drug Carrier Syst.,* 5:1-20, 1988.
Crickmore et al., *Abstr. 28th Annu. Meet. Soc. Invert. Pathol.*, Cornell University, Ithaca, N.Y., 1995.
Cristou et al., *Plant Physiol,* 87:671-674, 1988.

Curiel, Agarwal, Wagner, Cotten, "Adenovirus enhancement of transferrin-polylysine-mediated gene delivery," *Proc. Natl. Acad Sci. USA*, 88(19):8850-8854, 1991.

Curiel, Wagner, Cotten, Birnstiel, Agarwal, Li, Loechel, Hu, "High-efficiency gene transfer mediated by adenovirus coupled to DNA-polylysine complexes," *Hum. Gen. Ther.*, 3(2):147-154, 1992.

de Barjac, In: *Microbial Control of Pests and Plant Diseases*, H. D. Burges, ed., Academic Press, London, 36-43, 1981.

Donovan et al., *Appl. Environ. Microbiol.*, 58:3921-3927, 1992.

Donovan et al., *Mol. Gen. Genet.*, 214:365-372, 1988.

Eglitis and Anderson, "Retroviral vectors for introduction of genes into mammalian cells," *Biotechniques*, 6(7):608-614, 1988.

Eglitis, Kantoff, Kohn, Karson, Moen, Lothrop, Blaese, Anderson, "Retroviral-mediated gene transfer into hemopoietic cells," *Avd. Exp. Med. Biol.*, 241:19-27, 1988.

Eichenlaub, *J. Bacteriol.*, 138(2):559-566, 1979.

Fiers et al., *Nature*, 273:113, 1978.

Fraley et al., *Biotechnology*, 3:629, 1985.

Fraley et al., *Proc. Natl. Acad Sci. USA*, 80:4803, 1983.

Fromm, Taylor, Walbot, "Expression of genes transferred into monocot and dicot plant cells by electroporation," *Proc. Natl. Acad. Sci. USA*, 82(17):5824-5828, 1985.

Fujimura et al., *Plant Tissue Culture Letters*, 2:74, 1985.

Fynan, Webster, Fuller, Haynes, Santoro, Robinson, "DNA vaccines: protective immunizations by parenteral, mucosal, and gene gun inoculations," *Proc. Natl. Acad. Sci. USA* 90(24):11478-11482, 1993.

Gawron-Burke and Baum, *Genet. Engineer.*, 13:237-263, 1991.

Gefter et al., *Somat. Cell Genet.*, 3:231-236, 1977.

Gill et al., *J. Biol. Chem.*, 270:27277-27282, 1995.

Goding, *Monoclonal Antibodies: Principles and Practice*, pp. 60-74. 2nd Edition, Academic Press, Orlando, Fla., 1986.

Goeddel et al., *Nature*, 281:544, 1979.

Goeddel et al., *Nucl. Acids Res.*, 8:4057, 1980.

Graham and van der Eb, "Transformation of rat cells by DNA of human adenovirus 5," *Virology*, 54(2):536-539, 1973.

Green, *Nuc. Acids Res.* 16(1):369. 1988.

Grochulski et al., *J. Mol. Biol.*, 254:447-464, 1995.

Harlow and Lane, *Antibodies: A Laboratory Manual*, Cold Spring Harbor Laboratory, Cold Spring Harbor, N.Y., 1988.

Henry-Michelland et al., "Attachment of antibiotics to nanoparticles; Preparation, drug-release and antimicrobial activity in vitro," *Int. J. Pharm.*, 35:121-127, 1987.

Hermstadt et al., *Bio/Technology*, 4:305-308, 1986.

Herrnstadt et al., *Gene*, 57:37-46, 1987.

Hess et al., *J. Adv. Enzyme Reg.*, 7:149, 1968.

Hess, *Intern Rev. Cytol.*, 107:367, 1987.

Hilber, Bodmer, Smith, Koller, "Biolistic transformation of conidia of *Botryotinia fuckeliana*," *Curr. Genet.*, 25(2):124-127, 1994.

Hitzeman et al., *J. Biol. Chem.*, 255:2073, 1980.

Hofte and Whiteley, *Microbiol. Rev.*, 53:242-255, 1989.

Höfte et al., *Nucl. Acids Res.*, 15:7183, 1987.

Holland et al., *Biochemistry*, 17:4900, 1978.

Honee et al., *Mol. Microbiol.*, 5:2799-2806, 1991.

Hoover et al., (Eds.), *Remington's Pharmaceutical Sciences*, 15th Edition, Mack Publishing Co., Easton, Pa., 1975.

Horton et al., *Gene*, 77:61-68, 1989.

Itakura et al., *Science*, 198:1056, 1977.

Jameson and Wolf, "The Antigenic Index: A Novel Algorithm for Predicting Antigenic Determinants," *Compu. Appl. Biosci.*, 4(1):181-6, 1988.

Johnston and Tang, "Gene gun transfection of animal cells and genetic immunization," *Methods Cell. Biol.*, 43(A):353-365, 1994.

Jones, *Genetics*, 85:12 1977.

Jorgensen et al., *Mol. Gen. Genet.*, 207:471, 1987.

Keller et al., *EMBO J.*, 8:1309-14, 1989.

Kingsman et al., *Gene*, 7:141, 1979.

Klein et al., *Nature*, 327:70, 1987.

Klein et al., *Proc. Natl. Acad. Sci. USA*, 85:8502-8505, 1988.

Knight et al., *J. Biol. Chem.*, 270:17765-17770, 1995.

Kohler and Milstein, *Eur. J. Immunol.*, 6:511-519, 1976.

Kohler and Milstein, *Nature*, 256:495-497, 1975.

Korn and Queen, *DNA*, 3:421-436, 1984.

Kreig et al., *AnzSchaed. lingskde, Pflanzenschutz, Umwelrschulz*, 57:145-150, 1984.

Kreig et al., *In: Zangew Ent.*, 96:500-508, 1983.

Krieg et al., *J. Appl. Ent.*, 104:417-424, 1987.

Kuby, *In: Immunology 2nd Edition*, W. H. Freeman & Company, New York, 1994.

Kyte and Doolittle, "A simple method for displaying the hydropathic character of a protein," *J. Mol. Biol.*, 157(1):105-132, 1982.

Ladd Jr., *J. Econ. Entomol.*, 79:00668-671, 1986.

Lambert et al., *Appl. Environ. Microbiol.*, 58:2536-2642, 1992b.

Lambert et al., *Gene*, 110:131-132, 1992a.

Langridge et al., *Proc. Natl. Acad. Sci. USA*, 86:3219-3223, 1989.

Lee et al., *Biochem. Biophys. Res. Comm.*, 216:306-312, 1995.

Lindstrom et al., Developmental Genetics, 11: 160, 1990.

Lorz et al., *Mol. Gen. Genet.*, 199:178, 1985.

Lu, Xiao, Clapp, Li, Broxmeyer, "High efficiency retroviral mediated gene transduction into single isolated immature and replatable CD34(3+) hematopoietic stem/progenitor cells from human umbilical cord blood," *J. Exp. Med.* 178(6):2089-2096, 1993.

Luo et al., *Plant Mol. Biol. Reporter*, 6:165, 1988.

Macaluso and Mettus, *J. Bacteriol.*, 173:1353-1356, 1991.

Maddock et al., *Third International Congress of Plant Molecular Biology*, Abstract 372, 1991.

Maloy et al., "Microbial Genetics" 2nd Edition. Jones and Barlett Publishers, Boston, Mass., 1994.

Maloy, "Experimental Techniques in Bacterial Genetics" Jones and Bartlett Prokop, A., and Bajpai, R. K. "Recombinant DNA Technology 1" *Ann. N.Y. Acad. Sci.*, Vol. 646, 1991.

Maniatis et al., *In: Molecular Cloning: a Laboratory Manual*, Cold Spring Harbor Laboratory, Cold Spring Harbor, N.Y., 1982.

Marcotte et al., *Nature*, 335:454, 1988.

Masson et al., *J. Biol. Chem.*, 270:20309-20315, 1995.

McCabe et al., *Biotechnology*, 6:923, 1988.

McPherson et al., *Bio/Technology*, 6:61-66, 1988.

Mettus and Macaluso, *Appl. Environ. Microbiol.*, 56:1128-1134, 1990.

Neuhaus et al., *Theor. Appl. Genet.*, 75:30, 1987.

Norton et al., *Plasmid*, 13:211-214, 1985.

Odell et al., *Nature*, 313:810, 1985.

Omirulleh et al., *Plant Molecular Biology*, 21:415-428, 1993.

Pena et al., *Nature*, 325:274, 1987.

Poszkowski et al., *EMBO J.*, 3:2719, 1989.

Potrykus et al., *Mol. Gen. Genet.*, 199:183, 1985.

Poulsen et al., *Mol. Gen. Genet.*, 205:193-200, 1986.

Prokop and Bajpai, *Ann. N.Y Acad. Sci.* 646, 1991.

Rogers et al., *In: Methods For Plant Molecular Biology*, A. Weissbach and H. Weissbach, eds., Academic Press Inc., San Diego, Calif. 1988.

Rogers et al., *Meth. in Enzymol.,* 153:253-277, 1987.

Rupar et al., *Appl. Environ. Microbiol.,* 57:3337-3344, 1991.

Sambrook et al., *In: Molecular Cloning. A Laboratory Manual*, Cold Spring Harbor Laboratory, Cold Spring Harbor, N.Y., 1989.

Segal, *Biochemical Calculations,* 2nd Edition. John Wiley & Sons, New York, 1976.

Sekar et al. , *Proc. Natl. Acad Sci. USA,* 84:7036-7040, 1987.

Sick et al., *Nucl. Acids Res.,* 18:1305, 1990.

Simpson, *Science,* 233:34, 1986.

Southern, *J. Mol. Biol.,* 98:503-517, 1975.

Spielmann et al., *Mol. Gen. Genet.,* 205:34, 1986.

Toriyama et al., *Theor Appl. Genet.,* 73:16, 1986.

Uchimiya et al., *Mol. Gen. Genet.,* 204:204, 1986.

Van Tunen et al., *EMBO J.,* 7:1257, 1988.

Vasil et al., "Herbicide-resistant fertile transgenic wheat plants obtained by microprojectile bombardment of regenerable embryogenic callus," *Biotechnology,* 10:667-674, 1992.

Vasil, *Biotechnology,* 6:397, 1988.

Vodkin et al., *Cell,* 34:1023, 1983.

Wagner et al., "Coupling of adenovirus to transferrin-polylysine/DNA complexes greatly enhances receptor-mediated gene delivery and expression of transfected genes," *Proc. Natl. Acad. Sci. USA,* 89 (13):6099-6103, 1992.

Weissbach and Weissbach, *Methods for Plant Molecular Biology*, (eds.), Academic Press, Inc., San Diego, Calif., 1988.

Wenzler et al., *Plant Mol. Biol.,* 12:41-50, 1989.

Wolf et al., *Compu. Appl. Biosci.,* 4(1):187-911988.

Wong and Neumann, "Electric field mediated gene transfer," *Biochim. Biophys. Res. Commun.* 107(2):584-587, 1982.

Yamada et al., *Plant Cell Rep.,* 4:85, 1986.

Yang et al., *Proc. Natl. Acad. Sci. USA,* 87:4144-48, 1990.

Zatloukal, Wagner, Cotten, Phillips, Plank, Steinlein, Curiel, Bimstiel, "Transferrinfection: a highly efficient way to express gene constructs in eukaryotic cells," *Ann. N.Y. Acad. Sci.,* 660:136-153, 1992.

Zhou et al., *Methods in Enzymology,* 101:433, 1983.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are as described in the claims below.

The invention claimed is:

1. A purified antibody that binds to a CryET33 peptide, wherein the CryET33 peptide is SEQ ID NO:3.

2. The purified antibody of claim 1 generated by using a peptide according to SEQ ID NO:3 as an immunogen.

3. The purified antibody of claim 1 produced by a hybridoma, wherein a peptide according to SEQ ID NO:3 is used to generate the hybridoma producing the antibody.

4. A method for detecting a CryET33 peptide in a biological sample, comprising the steps of:

(a) obtaining a biological sample suspected of containing the peptide;

(b) contacting the sample with an antibody of claim 1, that binds to the peptide, under conditions effective to allow the formation of complexes; and (c) detecting the complexes so formed.

5. The method of claim 4, wherein the antibody is generated by using a peptide according to SEQ ID NO:3 as an immunogen.

6. An immunodetection kit comprising, in suitable container means, an antibody of claim 1 that binds to a CryET33 peptide, and an immunodetection reagent

7. The immunodetection kit of claim 6, wherein the antibody is generated by using a peptide of SEQ ID NO:3 as an immunogen.

* * * * *